US006962792B1

(12) United States Patent
Ball et al.

(10) Patent No.: US 6,962,792 B1
(45) Date of Patent: Nov. 8, 2005

(54) METHODS AND MEANS FOR INHIBITION OF CDK4 ACTIVITY

(75) Inventors: Kathryn Lindsay Ball, Dundee (GB); David Philip Lane, Fife (GB)

(73) Assignee: Cyclacel Limited, Scotland (GB)

( * ) Notice: Subject to any disclaimer, the term of this patent is extended or adjusted under 35 U.S.C. 154(b) by 0 days.

(21) Appl. No.: 09/180,269

(22) PCT Filed: May 8, 1997

(86) PCT No.: PCT/GB97/01250

§ 371 (c)(1), (2), (4) Date: Jul. 8, 1999

(87) PCT Pub. No.: WO97/42222

PCT Pub. Date: Nov. 13, 1997

(30) Foreign Application Priority Data

May 8, 1996 (GB) ................................ 960952
Oct. 9, 1996 (GB) ............................... 9621314

(51) Int. Cl.$^7$ ..................... G01N 33/53; G01N 33/569; G01N 33/566
(52) U.S. Cl. ......................... 435/7.8; 435/7.1; 435/7.2; 530/300
(58) Field of Search ........................... 435/7.1, 7.2, 7.8; 530/300

(56) References Cited

U.S. PATENT DOCUMENTS

| 5,424,400 A | 6/1995 | Smith et al. ................. 530/350 |
| 5,596,079 A | 1/1997 | Smith et al. ................. 530/328 |
| 5,672,508 A | 9/1997 | Gyuris et al. ............ 435/320.1 |
| 5,807,692 A | 9/1998 | Kinzler et al. ............. 437/7.21 |

FOREIGN PATENT DOCUMENTS

| EP | 0 002 805 | 12/1978 |
| FR | 2662698 | 12/1991 |
| WO | WO 93/1251 | 6/1993 |
| WO | WO 94/022167 | 2/1994 |
| WO | WO 94/09135 | 4/1994 |
| WO | WO-9409135 A1 * | 4/1994 |
| WO | WO 95/06415 | 3/1995 |
| WO | WO 95/13375 | 5/1995 |
| WO | WO 95/31995 | 11/1995 |
| WO | WO 96/14334 | 5/1996 |
| WO | WO 96/35715 | 11/1996 |
| WO | WO 97/03681 | 2/1997 |
| WO | WO 97/42222 | 11/1997 |

OTHER PUBLICATIONS

Voet et al. Biochemistry. 1990. John Wiley & Sons, Inc., pp. 126–128 and 228–234.*
Xiong et al. p21 is a universal inhibitor of cyclin kinases. Nature. vol. 366, pp. 701–704. 1993.*
Ball, Kathryn L. et al. (1996) "Cell–Cycle Arrest And Inhibition Of Cdk4 Activity By Small Peptides Based On The Carboxy–Terminal Domain Of p21$^{WAF1}$" Current Biology, vol. 7 pp. 71–80.

Ball, Kathryn L. et al. (1996) "Human And Plant proliferating–Cell Nuclear Antigen Have A highly Conserved Binding Site For The p53–Inducible Gene product p21$^{WAF1}$" Eur. J. Biochem. vol. 237 pp. 854–861.
Chen, Junjie et al. (1996) "p21$^{Cip1/Waf1}$ Disrupts The Recruitment Of Human Fen1 By Proliferating–Cell Nuclear Antigen Into The DNA Replication Complex" Proc. Natl. Acad. Sci. USA, vol. 93, pp. 11597–11602.
Chen, Junjie et al. (1996) "Cyclin–Binding Motifs Are Essential For The Function of p21$^{CIP1}$" Molecular and Cellular Biology, vol. 16, No. 9 pp. 4673–4682.
Chen, Junjie et al. (1995) "Separate Domains Of p21 Involved in The Inhibition Of Cdk Kinase And PCNA", Nature, Nature, vol. 374, pp. 386–388.
Chen, I–Tsuen et al. (1996) "Characterization of p21$^{Cip1/Waf1}$ Peptide Domains Required For Cyclin E/Cdk2 and PCNA Interaction" Oncogene vol. 12 pp. 595–607.
Deng, Chuxia et al. (1995) "Mice Lacking p21$^{Cip1/Waf1}$ Undergo Normal Development, But Are Defective In G1 Checkpoint Control", Cell, vol. 82, pp. 675–684.
Eastham, James A. et al. (1995) "In Vivo Gene Therapy with p53 or p21 Adenovirus For Prostate Cancer", Cancer Research, vol. 55, pp. 5151–5155.
El–Deiry, Wafik S. et al. (1993) "WAF1, A Potential Mediator Of p53 Tumor Suppression" Cell, vol. 75, pp. 817–825.
Goubin, Francoise et al. (1995) "Identification of Binding Domains on the p21$^{Cip1}$Cyclin–Dependent Kinase Inhibitor" Oncogene, vol. 10, pp. 2281–2287.
Gu, Yong et al. (1993) "Inhibition Of CDK2 Activity In Vivo By An Associated 20 K Regulatory Subunit" Nature, vol. 366, pp. 707–710.
Harper, J. Wade et al. (1995) "Inhibition Of Cyclin–Dependent Kinases By p21", Molecular Biology of the Cell, vol. 6, pp. 387–400.
Harper, J. Wade et al. (1993) "The p21 Cdk–Interacting Protein Cip1 Is A Potent Inhibitor Of G1 Cyclin–Dependent Kinases", Cell, vol. 75, pp. 805–816.
Hiraoka, Lea R. et al. (1995) "Sequence Of Human FEN–1, A Structure–Specific Endonuclease, And Chromosomal Localization Of The Gene (FEN1) In Mouse And Human" Genomics vol. 25, pp. 220–225.
Lin, Jiayuh et al. (1996) "Analysis of Wild–Type and Mutant p21$^{WAF-1}$ Gene Activities" Molecular and Cellular Biology, vol. 16, No. 4, pp. 1786–1793.

(Continued)

*Primary Examiner*—Joseph Murphy
(74) *Attorney, Agent, or Firm*—Lahive & Cockfield, LLP; Giulio A. DeConti, Jr.; Cynthia L. Kanik

(57) ABSTRACT p21$^{WAF1}$ interacts with cyclin D1 and Cdk4. Peptide fragments of p21 inhibit the interaction and/or affect Cdk4 activity. The peptides, derivative peptides and non-peptidyl mimetics thereof are useful in affecting activity of Cdk4, such as RB phosphorylation, and cellular proliferation, indicative of therapeutic usefulness in treatment of tumours and other hyperproliferative disorders. Assay and screening methods allow identification of such modulators, especially inhibitors, of Cdk4 activity.

26 Claims, 10 Drawing Sheets

OTHER PUBLICATIONS

Figures 1A, 1B:
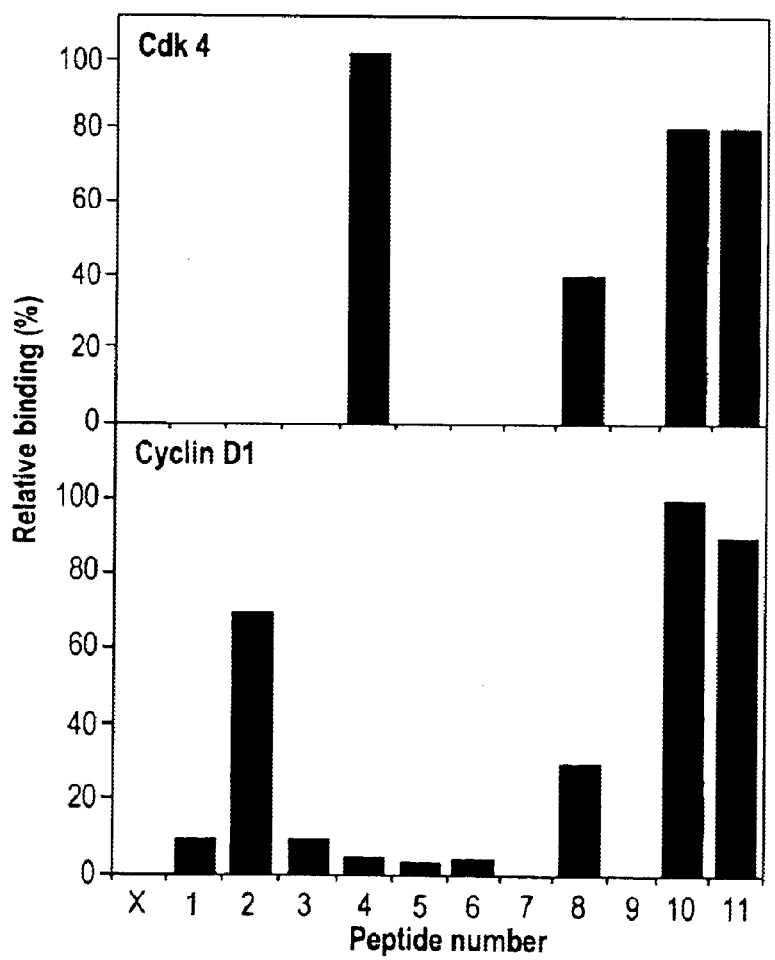

Luo, Yan et al. (1995) "Cell–cycle Inhibition by Independent CDK and PCNA Binding domains In p21$^{Cip1}$" Nature vol. 375, pp. 159–161.

MacLachlan, Timohty K. (1995) "Cyclins, Cyclin–Dependent Kinases And Cdk Inhibitors: Implications In Cell Cycle Control And Cancer" Critical Reviews in Eukaryotic Gene Expression, vol. 5, No. 2, pp. 127–156.

Nakanishi, Makoto et al. (1995) "The C–Terminal Region Of p21$^{SDI1/WAF1/CIP1}$ Is Involved In Proliferating Cell Nuclear Antigen Binding But Does Not Appear To Be Required For Growth Inhibition" The Journal of biological Chemistry, vol. 270, No. 29, pp. 17060–17063.

Nakanishi, Makoto et al. (1995) "Identification Of The Active Region Of The DNA Synthesis Inhibitory Gene p21$^{SDI1/CIP1/WAF1}$" The EMBO Journal, vol. 14, No. 3, pp. 555–563.

Flores–Rozas, Hernan et al. (1994) "Cdk–Interacting Protein 1 Directly Binds With Proliferating Cell Nuclear Antigen And Inhibits DNA Replication Catalyzed By The DNA Polymerase δ Holoenzyme" Proc. Natl. Acad. Sci. USA, vol. 92, pp. 8655–6859.

Su, Jin–Yuan et al. (1995) "Cloning And Characterizatin Of The Xenopus Cyclin–Dependent Kinase Inhibitor p27$^{XIC1}$" Proc. Natl. Acad. Sci. USA, vol. 92, pp. 10187–10191.

Waga, Shou et al. (1994) "The p21 Inhibitor Of Cyclin–Dependent Kinases Controls DNA Replication By Interaction With PCNA" Nature vol. 369, pp. 574–578.

Waldman, Todd et al. (1995) "p21 Is necessary For The p53–Mediated $G_1$ Arrest In Human Cance Cells" Cancer Research, vol. 55, pp. 5187–5190.

Warbrick, Emma et al. (1995) "A Small Peptide Inhibitor Of DNA Replication Defines The Site Of Interaction Between The Cyclin–Dependent Kinase Inhibitor p21$^{WAF1}$ And proliferating Cell Nuclear Antigen" Current Biology, vol. 5 No. 3, pp. 275–282.

Warbrick, Emma et al. (1997) "Homologous Regions of Fen1 and p21$^{Cip1}$ Compete For Binding To The Same Site On PCNA: A Potential Mechanism To Co–Ordinate DNA Replication And Repair" Oncogene, vol. 14, pp. 2313–2321.

Xiong, Yue et al. (1993) "p21 Is A Universal Inhibitor Of Cyclin Kinases" Nature vol. 366, pp. 701–704.

Zhang, Hui et al. (1994) "p21–Containing Cyclin Kinases Exist In Both Active And Inactive States" Genes & Development, vol. 8, pp. 1750–1758.

Adams, Peter D. et al. "Identification of a Cyclin–cdk2 Recognition Motif Present in Substrates and p21–Like Cyclin–Dependent Kinase Inhibitors" *Molecular and Cellular Biology* 16:6623–6633 (Dec. 1996).

* cited by examiner

| | | |
|---|---|---|
| Peptide 1 | M S E P A G D V R Q N P C G S K A C R R |
| Peptide 2. | K A C R R L F G P V D S E Q L S R D C D |
| Peptide 3. | S R D C D A L M A G C I Q E A R E R W N |
| Peptide 4. | R E R W N F D F V T E T P L E G D F A W |
| Peptide 5. | G D F A W E R V R G L G L P K L Y L P T |
| Peptide 6. | L Y L P T G P R R G R D E L G G G R R P |
| Peptide 7. | G G R R P G T S P A L L Q G T A E E D H |
| Peptide 8. | A E E D H V D L S L S C T L V P R S G E |
| Peptide 9. | P R S G E Q A E G S P G G P G D S Q G R |
| Peptide 10. | K R R Q T S M T D F Y H S K R R L I F S |
| Peptide 11. | T S M T D F Y H S K R R L I F S K R K P |

```
          a -     PRSGEQAEGSPGGPGDSQGR
          b -         EQAEGSPGGPGDSQGRKRRQ
          c -             GSPGGPGDSQGRKRRQTSMT
          d -                 GPGDSQGRKRRQTSMTDFYH
          e -                     SQGRKRRQTSMTDFYHSKRR
peptide  10 -                         KRRQTSMTDFYHSKRRLIFS
          f -                             TSMTDFYHSKRRLIFSKRKP
          g -                                 DFYHSKRRLIFSKRKP
```

*Fig. 5*

| Peptide/protein | $I_{0.5}$ |
|---|---|
| p16$^{INK4}$-peptide (■) | 16.3 μM |
| 10 (○) | 0.1 μM |
| Asp→Ala mutant (●) | 46 nM |
| Full-length p21$^{WAF1}$ (▼) | 11 nM |

Peptide I    KRRQTSATDFYHSKRRLIFS|RQIKIWFQNRRMKWKK|

Peptide II   KRRLIFSK|RQIKIWFQNRRMKWKK|

Peptide III  RQTSMTDFYHSKRR|RQIKIWFQNRRMKWKK|

| Phase | Cell-cycle distribution (%) | | | |
|---|---|---|---|---|
| | MRC5 | | MCF7 | |
| | Control | Peptide I | Control | Peptide I |
| G1 | 37 | 66 | 42 | 68 |
| S | 38 | 14 | 36 | 16 |
| G2/M | 16 | 13 | 12 | 10 |

SEQUENCE LISTING

```
<160> NUMBER OF SEQ ID NOS:  28

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 1

Met Ser Glu Pro Ala Gly Asp Val Arg Gln Asn Pro Cys Gly Ser Lys
 1               5                   10                  15

Ala Cys Arg Arg
            20
```

```
<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 2

Lys Ala Cys Arg Arg Leu Phe Gly Pro Val Asp Ser Glu Gln Leu Ser
 1               5                  10                  15

Arg Asp Cys Asp
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 3

Ser Arg Asp Cys Asp Ala Leu Met Ala Gly Cys Ile Gln Glu Ala Arg
 1               5                  10                  15

Glu Arg Trp Asn
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 4

Arg Glu Arg Trp Asn Phe Asp Phe Val Thr Glu Thr Pro Leu Glu Gly
 1               5                  10                  15

Asp Phe Ala Trp
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 5

Gly Asp Phe Ala Trp Glu Arg Val Arg Gly Leu Gly Leu Pro Lys Leu
 1               5                  10                  15

Tyr Leu Pro Thr
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 6

Leu Tyr Leu Pro Thr Gly Pro Arg Arg Gly Arg Asp Glu Leu Gly Gly
 1               5                  10                  15

Gly Arg Arg Pro
            20
```

-continued

```
<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 7

Gly Gly Arg Arg Pro Gly Thr Ser Pro Ala Leu Leu Gln Gly Thr Ala
  1               5                  10                  15

Glu Glu Asp His
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 8

Ala Glu Glu Asp His Val Asp Leu Ser Leu Ser Cys Thr Leu Val Pro
  1               5                  10                  15

Arg Ser Gly Glu
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 9

Pro Arg Ser Gly Glu Gln Ala Glu Gly Ser Pro Gly Gly Pro Gly Asp
  1               5                  10                  15

Ser Gln Gly Arg
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 10

Lys Arg Arg Gln Thr Ser Met Thr Asp Phe Tyr His Ser Lys Arg Arg
  1               5                  10                  15

Leu Ile Phe Ser
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 11

Thr Ser Met Thr Asp Phe Tyr His Ser Lys Arg Arg Leu Ile Phe Ser
  1               5                  10                  15

Lys Arg Lys Pro
```

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Motif

<400> SEQUENCE: 12

Arg Arg Leu Ile Phe
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Motif

<400> SEQUENCE: 13

Lys Arg Arg Leu Ile Phe Ser Lys
 1               5

<210> SEQ ID NO 14
<211> LENGTH: 9
<212> TYPE: PRT
<213> ORGANISM: Artificial Sequence
<220> FEATURE:
<221> NAME/KEY: SITE
<222> LOCATION: (2)..(3)
<223> OTHER INFORMATION: Xaa may be any amino acid
<221> NAME/KEY: SITE
<222> LOCATION: 6, 8
<223> OTHER INFORMATION: Xaa may be hydrophobic
<221> NAME/KEY: SITE
<222> LOCATION: 1, 9
<223> OTHER INFORMATION: Residue may be absent or different, ie another
      amino acid
<223> OTHER INFORMATION: Description of Artificial Sequence: General
      formula

<400> SEQUENCE: 14

Lys Xaa Xaa Arg Arg Xaa Phe Xaa Pro
 1               5

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Carrier
      peptide

<400> SEQUENCE: 15

Arg Gln Ile Lys Ile Trp Phe Gln Asn Arg Arg Met Lys Trp Lys Lys
 1               5                  10                  15

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 16

Pro Arg Ser Gly Glu Gln Ala Glu Gly Ser Pro Gly Gly Pro Gly Asp
 1               5                  10                  15
```

-continued

```
Ser Gln Gly Arg
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 17

Glu Gln Ala Glu Gly Ser Pro Gly Gly Pro Gly Asp Ser Gln Gly Arg
 1               5                  10                  15

Lys Arg Arg Gln
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 18

Gly Ser Pro Gly Gly Pro Gly Asp Ser Gln Gly Arg Lys Arg Arg Gln
 1               5                  10                  15

Thr Ser Met Thr
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 19

Gly Pro Gly Asp Ser Gln Gly Arg Lys Arg Arg Gln Thr Ser Met Thr
 1               5                  10                  15

Asp Phe Tyr His
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 20

Ser Gln Gly Arg Lys Arg Arg Gln Thr Ser Met Thr Asp Phe Tyr His
 1               5                  10                  15

Ser Lys Arg Arg
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 21

Thr Ser Met Thr Asp Phe Tyr His Ser Lys Arg Arg Leu Ile Phe Ser
 1               5                  10                  15
```

```
Lys Arg Lys Pro
            20

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthesised

<400> SEQUENCE: 22

Asp Phe Tyr His Ser Lys Arg Arg Leu Ile Phe Ser Lys Arg Lys Pro
 1               5                  10                  15

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Truncated
      peptide

<400> SEQUENCE: 23

Lys Arg Arg Leu Ile Phe Ser Lys
 1               5

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthesised

<400> SEQUENCE: 24

Lys Arg Arg Gln Thr Ser Ala Thr Asp Phe Tyr His Ser Lys Arg Arg
 1               5                  10                  15

Leu Ile Phe Ser Arg Gln Ile Lys Ile Trp Phe Gln Asn Arg Arg Met
                20                  25                  30

Lys Trp Lys Lys
         35

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthesised

<400> SEQUENCE: 25

Lys Arg Arg Leu Ile Phe Ser Lys Arg Gln Ile Lys Ile Trp Phe Gln
 1               5                  10                  15

Asn Arg Arg Met Lys Trp Lys Lys
                20

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthesised

<400> SEQUENCE: 26

Arg Gln Thr Ser Met Thr Asp Phe Tyr His Ser Lys Arg Arg Arg Gln
 1               5                  10                  15
```

-continued

```
Ile Lys Ile Trp Phe Gln Asn Arg Arg Met Lys Trp Lys Lys
             20                  25                  30

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthesised

<400> SEQUENCE: 27

Gln Thr Ser Met Thr Asp Phe Tyr
  1               5

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthesised

<400> SEQUENCE: 28

Lys Arg Arg Gln Thr Ser Ala Thr Asp Phe Tyr His Ser Lys Arg Arg
  1               5                  10                  15

Leu Ile Phe Ser
             20
```

METHODS AND MEANS FOR INHIBITION OF CDK4 ACTIVITY

The present invention relates to substances and their therapeutic use, and in particular to the identification of regions of p21$^{WAF1}$ that bind to cyclin dependent kinases, specifically Cdk4, and/or cyclin D1, and to substances, fragments and mimetics based on this region. The present invention also relates to pharmaceutical compositions comprising these molecules and their use in therapeutic applications for treating hyperproliferative disorders, such as cancer and psoriasis, and compositions comprising these molecules and their use in applications relating to growth in eukaryotic cells The invention also relates to assay methods and means for identifying substances useful for interfering with p21/Cdk4/cyclin interaction, and preferably inhibiting Cdk4 activity.

The tumour suppressor function of p53 is linked to a DNA-damage inducible cell cycle checkpoint pathway (Kastan et al., 1991), in which p53 can induce either growth arrest (Agarwal et al., 1995) or apoptosis (Clarke et al., 1993; Lowe et al., 1993; Merritt et al., 1994) in the damaged cells. The biochemical activity of p53 most tightly associated with tumour suppression and growth arrest involves an ionising radiation-dependent activation of sequence-specific transcriptional activity (Kastan et al., 1991; Lu and Lane, 1993; Pietenpol, et al., 1994). p53 induces the transcription of a number of genes, the products of which play a direct role in mediating growth arrest. These p53-inducible negative regulators of cell proliferation include: the cyclin dependent kinase inhibitor (CKI), p21$^{WAF1}$ (El-Deiry et al., 1993; Harper et al., 1993; Xiong et al., 1993; Gu et al., 1993);.an apoptosis promoting protein, Bax (Miyashita and Reed, 1995); the insulin growth factor binding protein IGF-BP3 (Buckbinder et al., 1995); and Gadd45 (Kastan et al., 1992), a potent inhibitor of cell proliferation with an as yet unclear biochemical function (Kearsey et al., 1995).

A common event in the development of human neoplasia is the inactivation of a DNA damage-inducible cell cycle checkpoint pathway regulated by p53 (Hollstein et al., 1991; Lane, 1992; Agrawal et al., 1995). A variety of mechanisms can lead to the functional inactivation of the p53 pathway, including: missense mutations within, or deletions of the p53 gene, inactivation of wild type p53 protein function by interaction with the oncogenic cellular protein mdm-2 (Momand et al., 1992), or the inability to induce downstream effector molecules, such as p21$^{WAF1}$ (Deng et al., 1995; Waldman et al., 1995).

Our growing knowledge of the molecular mechanisms underlying the transformation of mammalian cells offers the opportunity to create rationally designed inhibitors of specific biochemical processes essential to uncontrolled cell proliferation or cancer. Recent developments have shown that the reactivation of the p53 pathway in some human tumours could in theory be achieved by: (i) activating the biochemical function of mutant p53 protein (Halazonetis and Kandil, 1993; Hupp et al., 1993), possibly using small peptides as leads for drug design (Hupp et al., 1995); (ii) disrupting the interaction of the oncogene mdm-2 and wild type p53 through the use of peptide-mimetic inhibitors of complex formation (Picksley et al., 1994); (iii) restoring or mimicking the function of the downstream effector molecule p21$^{WAF1}$, which on its own is capable of mediating growth suppression (El-Deiry et al., 1993; Eastham et al., 1995).

p21$^{WAF1}$ is an inhibitor of both the G1 cyclin dependent protein kinases (CDKs; which control the progression from G1 into S phase) (Harper et al., 1995) and proliferating cell nuclear antigen (PCNA; an essential DNA-replication factor) (Florez-Rozas et al., 1994; Waga et al., 1994). Thus, inhibition of the function of either CDKs or PCNA provides, in theory, two distinct avenues for development of drug discovery programmes which are based on the activity of p21$^{WAF1}$. The PCNA binding function of p21$^{WAF1}$ can be mimicked by a 20-amino acid peptide derived from the C-terminal domain of p21$^{WAF1}$ and this peptide is sufficient to partially inhibit SV40 replication in vitro (Warbrick et al., 1995).

Despite its PCNA binding role, the primary function of the p21$^{WAF1}$ protein as a growth suppressor appears to be inhibition of the G1 cyclin-CDK complexes (Chen et al., 1995; Harper et al., 1995; Luo et al., 1995; Nakanishi et al., 1995b). Luo et al. (1995) reported the N-terminal domain of p21, composed of residues 1–75, to act as a CDK-inhibitor in vitro, inhibiting cyclin E-Cdk2.

The present invention concerns (i) the elucidation of the molecular mechanism of cyclin D1-Cdk4 complex inhibition by p21$^{WAF1}$, and (ii) the identification of peptide mimetics of p21$^{WAF1}$ inhibitory activity, through the examination of the binding and inhibitory properties of a series of synthetic peptides based on the amino acid sequence of p21$^{WAF1}$. Our studies found that two peptides derived from the N-terminal domain of p21$^{WAF1}$ have biochemical activity; a peptide 4 (residues 46–65) forms a stable complex with Cdk4, but has no inhibitory activity, while a peptide 2 (residues 16–35) binds to cyclin D1 and inhibits Cdk4 activity with a I0.5 of 2 $\mu$M.

These data define for a cyclin binding site on p21$^{WAF1}$ and suggest that one mechanism involved in the CDK inhibitory action of p21$^{WAF1}$ employs binding to the cyclin subunit of the CDK holoenzyme. This has lead us to propose that p21$^{WAF1}$ can inhibit Cdk4 activity allosterically through conformational or (ii) interfering with the cyclin-Cdk interaction or (iii) interfering with the cyclin-Cdk-substrate interaction changes in the structure of cyclin D1. Furthermore, peptides based on the C-terminal sequence of p21$^{WAF1}$ interact with both cyclin D1 and Cdk4, and are potent inhibitors of Cdk4 activity, with a peptide (peptide 10 herein) composed of residues 141–160 having an I$_{0.5}$ of 0.1 $\mu$M. We show that both of the inhibitory peptides bind at physiologically relevant sites on cyclin D1 and/or Cdk4, and that they display specificity mimicking that of full length p21$^{WAF1}$. Importantly, the potency of the C-terminal peptide is improved by making a single amino acid substitution (D-A at position 149). We have mapped the inhibitory component of this peptide using alanine mutation analysis and show that it is distinct from the PCNA interaction domain, which also resides in the C-terminal region of the p21$^{WAF1}$ protein.

Remarkably, a stretch of just five amino acids contains the Cdk4 inhibitory motif and a single conservative mutation at either of two hydrophobic amino acid residues completely abolishes the inhibitory activity of the peptide. These data have exciting implications for the mechanism of action of p21$^{WAF1}$ protein and represent a starting point for a drug design programme aimed at producing synthetic molecules functioning as tumour suppressors downstream of p53.

Accordingly, in one aspect, the present invention provides a substance which has the property of inhibiting Cdk4, said substance comprising:
(i) a peptide fragment consisting of the motif xyLzF, wherein y and z are any amino acid and x is preferably R, or a derivative of said peptide fragment; or,
(ii) a functional mimetic of said peptide fragment.

In a further aspect, the present invention provides the above substance for use in a method of medical treatment.

In a further aspect, the present invention provides the use of a substance which has the property of inhibiting Cdk4 in the preparation of a medicament for the treatment of a hyperproliferative disorder, said substance comprising:

(i) fragment of the C-terminal portion of p21$^{WAF1}$, or an active portion or derivative thereof; or, (ii) a peptide fragment including the motif xyLzF, wherein y and z are any amino acid and x is preferably R, or a derivative of said peptide fragment; or, (iii) a functional mimetic of (i) or (ii).

Figure 6:
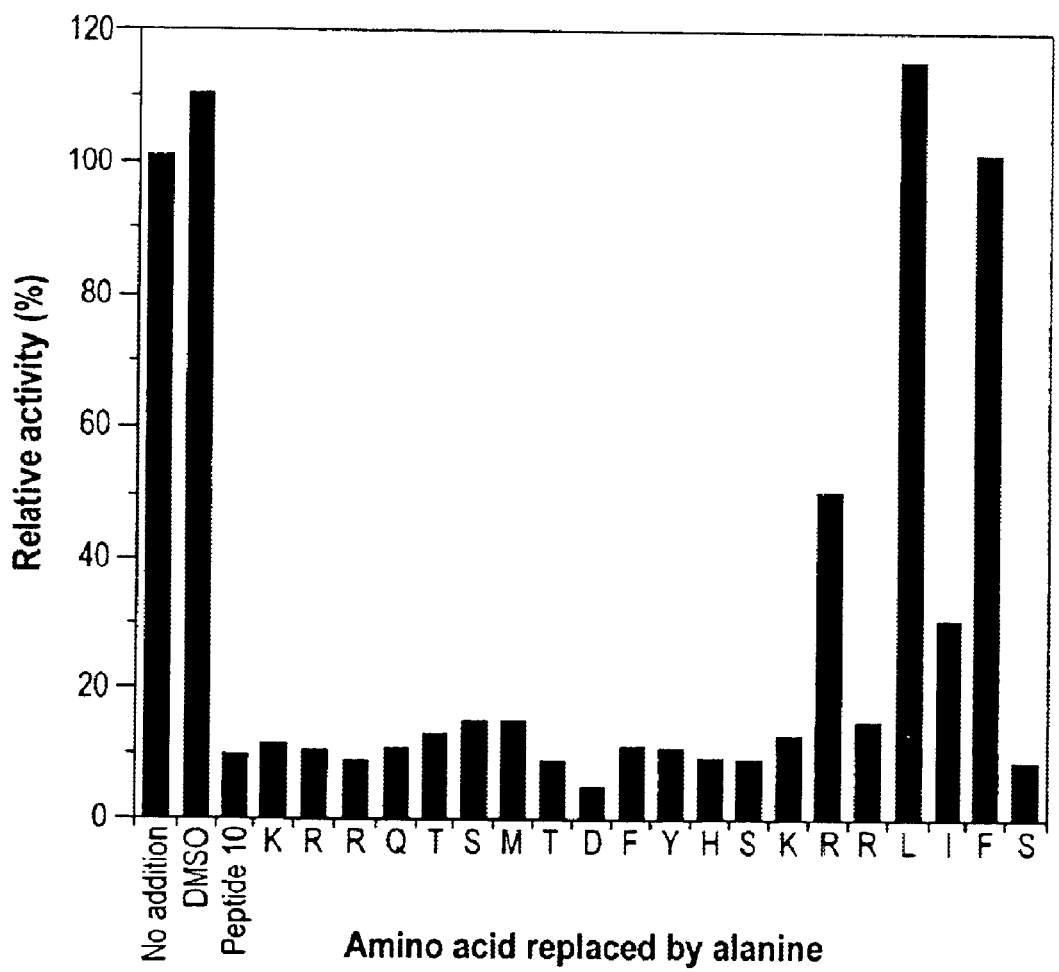

In a preferred embodiment, the C-terminal portion of p21$^{WAF1}$ consisting of the peptide motif KRRLIFSK (SEQ ID NO:13) as found to completely inhibit cyclin-Cdk4 activity and to prevent phosphorylation of pRb (see FIG. 6).

In a further aspect, the present invention provides a substance which has the property of binding to Cdk4 for use in a method of medical treatment, said substance comprising:

(i) a fragment of the p21$^{WAF1}$ protein consisting of residues 46–65 of the p21$^{WAF1}$ amino acid sequence, or an active portion or derivative thereof; or, (ii) a functional mimetic of said fragment.

In a further aspect, the present invention provides the use of a substance which has the property of binding Cdk4 in the preparation of a medicament for the treatment of a hyperproliferative disorder, said substance comprising:

(i) a fragment of the p21$^{WAF1}$ protein consisting of residues 46–65 of the p21$^{WAF1}$ amino acid sequence, or an active portion or derivative thereof; or, (ii) a functional mimetic of said fragment.

In a further aspect, the present invention provides a substance which has the properties of binding cyclin D and/or inhibiting Cdk4 for use in a method of medical treatment, said substance comprising:

(i) a fragment of the p21$^{WAF1}$ protein consisting of residues 16–35 of the p21$^{WAF1}$ amino acid sequence, or an active portion or derivative thereof; or, (ii) a functional mimetic of said fragment.

In a further aspect, the present invention provides the use of a substance which has the property of binding cyclin D1 and/or inhibiting Cdk4 in the preparation of a medicament for the treatment of a hyperproliferative disorder, said substance comprising:

(i) a fragment of the p21$^{WAF1}$ protein consisting of residues 16–35 of the p21$^{WAF1}$ amino acid sequence, or an active portion or derivative thereof; or, (ii) a functional mimetic of said peptide fragment.

Based on experimental evidence included below showing residues involved in binding of peptide 2 (residues 16–35), and the crystal structure available for p27 (related to p21), the following general formula for peptides useful in accordance with various aspects of the present invention is provided:

KxxRRyFxP(SEQ ID NO:14)

wherein x may be any amino acid, y and z may be hydrophobic, and each of the underlined residues may be absent or different, i.e. another amino acid. Hydrophobic residues may be alanine, valine, leucine, isoleucine, proline, phenylalanine, tryptophan, methionine. Either or both of the amino acids R may be substituted by other basic residues, particularly lysine (K) or histidine (H).

In the present invention, "an active portion" means a peptide which is less than the fragment of the p21$^{WAF1}$ amino acid sequence, but which retains the relevant property mentioned above.

In the present invention, "functional mimetic" means a substance which may not contain an active portion of the p21$^{WAF1}$ amino acid sequence and is probably not a peptide at all, but which has the relevant property mentioned above.

In the present invention, "a derivative" means a peptide modified by varying its amino acid sequence, eg by manipulation of the nucleic acid encoding the peptide or by altering the peptide itself. Such derivatives of the natural amino acid sequence may involve insertion, addition, deletion or substitution of one or more amino acids, without fundamentally altering the essential activity of the peptides. An example of a derivative is the p21WAF1 mutant in which A was substituted for D at position 149 of the full length protein, this mutant having enhanced cyclin D1-Cdk4 inhibitory activity.

Preferred substances according to certain embodiments of the present invention do not bind PCNA, and/or do not interfere with p21 interaction or binding with PCNA.

Cell cycle arrest may be induced by various aspects according to the present invention in Rb negative and/or Rb positive calls, as exemplified experimentally below.

In a further aspect, the present invention provides pharmaceutical compositions comprising one or more of the above substances in combination with a pharmaceutically acceptable carrier.

In a further aspect, the present invention relates to compositions comprising one or more of the above substances and their use in controlling the growth of eukaryotic cells, eg as a food preservative or as an agent to promote the growth of plants.

In a further aspect, the present invention provides compounds comprising any of the above substances coupled to carrier molecules, enabling the compounds to be delivered to cells in vivo. In one embodiment, the carrier molecule is a 16 aa peptide sequence derived from the homeodomain of Antennapedia (e.g. as sold under the name "Penetratin") which can be coupled to one of the above substances via a terminal Cys residue. Alternatively, as in the examples described below, a carrier peptide (having the sequence RQIKIWFQNRRMKWKK)(SEQ ID NO:5) can be synthesised so it is directly attached to peptide fragments. The "Penetratin" molecule and its properties are described in WO91/18981.

Thus, the present invention in various aspects provides for interfering with or interrupting interaction between p21 and cyclin D1 and/or Cdk4 using an appropriate agent.

Such an agent may be capable of blocking binding between a site located at amino acid residues identified herein as being involved in and/or important for binding or interaction with cyclin D1 and/or Cdk4.

The full sequence of the p21 protein has been elucidated and is set out in WO095/13375, WO93/12251 and WO95/06415 which are incorporated herein by reference.

Such agents may be identified by screening techniques which involve determining whether an agent under test inhibits or disrupts the binding of p21 protein or a suitable fragment, derivative, analogue or functional mimetic thereof, with cyclin D1 and/or Cdk4, or a relevant fragment, derivative, analogue or functional mimetic thereof.

Suitable fragments of p21 include those which include residues as identified herein. Smaller fragments, and derivatives, analogues and functional mimetics of this fragment may similarly be employed, e.g. pepcides identified using a technique such as alanine scanning.

In a further aspect of the invention, whereas assays using the peptides described herein and the use of the peptides are described in the context of modulating the interaction of p21 with cyclin D1 and/or Cdk4, these peptides may also be useful as p21 mimetics to inhibit the interaction of p21 and other cyclin-Cdk interactions, particularly G1 complexes such as cyclin E-Cdk2. Thus the various described embodiments of the invention above and below herein with regard to cyclin D1 and/or Cdk4 is applicable mutatis mutandis to these other cyclins and/or Cdks respectively.

Screening methods and assays are discussed in further detail below.

One class of agents that can be used to disrupt the binding of p21 and cyclin D1 and/or Cdk 4 are peptides based on the sequence motifs of p21 that interact with cyclin D1 and/or Cdk4. Such peptides tend to be small molecules, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6 5 or less in length. The present invention also encompasses peptides which are sequence variants or derivatives of a wild type p21 sequence.

Preferably, the amino acid sequence shares homology with a fragment of the relevant p21 fragment sequence shown preferably at least about 30%, or 40%, or 50%, or 60%, or 70%, or 75%, or 80%, or 85% homology, or at least about 90% or 95% homology. Thus, a peptide fragment of p21 may include 1, 2, 3, 4, 5, greater than 5, or greater than 10 amino acid alterations such as substitutions with respect to the wild-type sequence.

A derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of p21. 1, 2, 3, 4 or 5 or more additional amino acids, adjacent to the relevant specific peptide fragment in p21, or heterologous thereto may be included at one end or both ends of the peptide.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Homology may be over the full-length of the relevant peptide or over a contiguous sequence of about 5, 10, 15, 20, 25, 30 or 35 amino acids, compared with the relevant wild-type amino acid sequence.

As noted, variant peptide sequences and peptide and non-peptide analogues and mimetics may be employed, as discussed further below.

Various aspects of the present invention provide a substance, which may be a single molecule or a composition including two or more components, which includes a peptide fragment of p21 which includes a sequence as recited above and/or disclosed elsewhere herein, a peptide consisting essentially of such a sequence, a peptide including a variant, derivative or analogue sequence, or a non-peptide analogue or mimetic which has the ability to bind cyclin D1 and/or Cdk4 and/or disrupt or interfere with interaction between p21 and cyclin D1 and/or Cdk4.

Variants include peptides in which individual amino acids can be substituted by other amino acids which are closely related as is understood in the art and indicated above.

Non-peptide mimetics of peptides are discussed further below.

As noted, a peptide according to the present invention and for use in various aspects of the present invention may include or consist essentially of a fragment of p21 as disclosed, such as a fragment whose sequence is given above. Where one or more additional amino acids are included, such amino acids may be from p21 or may be heterologous or foreign to p21. A peptide may also be included within a larger fusion protein, particularly where the peptide is fused to a non-p21 (i.e. heterologous or foreign) sequence, such as a polypeptide or protein domain.

The invention also includes derivatives of the peptides, including the peptide linked to a coupling partner, e.g. an effector molecule, a label, a drug, a toxin and/or a carrier or transport molecule. Techniques for coupling the peptides of the invention to both peptidyl and non-peptidyl coupling partners are well known in the art. In one embodiment, the carrier molecule is a 16 aa peptide sequence derived from the homeodomain of *Antennapedia* (e.g. as sold under the name "Penetratin"), which can be coupled to a peptide via a terminal Cys residue. The "Penetratin" molecule and its properties are described in WO 91/18981.

Peptides may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a peptidyl molecule according to the present invention (peptide or polypeptide) is to express nucleic acid encoding it, by use of nucleic acid in an expression system.

Accordingly the present invention also provides in various aspects nucleic acid encoding the polypeptides and peptides of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequences for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide or peptide in accordance with the present invention can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding p21 fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the p21 sequences can be made, e.g. using site directed mutagenesis, to lead to the expression of modified p21 peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of E. coli, yeast, and eukaryotic cells such as COS or CHO cells.

Thus, the present invention also encompasses a method of making a polypeptide or peptide (as disclosed), the method including expression from nucleic acid encoding the polypeptide or peptide (generally nucleic acid according to the invention). This may conveniently be achieved by growing a host cell in culture, containing such a vector, under appropriate conditions which cause or allow expression of the polypeptide. Polypeptides and peptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acid as disclosed herein.

The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid encoding a peptidyl molecule according to the present invention may take place in vivo by way of gene therapy, to disrupt or interfere with interaction between p21 and cyclin D1 and/or ckd4.

Thus, a host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) Also, the presence of a mutant, allele, derivative or variant sequence within cells of an organism, particularly when in place of a homologous endogenous sequence, may allow the organism to be used as a model in testing and/or studying substances which modulate activity of the encoded polypeptide in vitro or are otherwise indicated to be of therapeutic potential. Conveniently, however, assays for such substances may be carried out in vitro, within host cells or in cell-free systems.

Suitable screening methods are conventional in the art. They include techniques such as radioimmunosassay, scintillation proximetry assay and ELISA methods. Suitably either the p21 protein or fragment or cyclin D1 and/or Cdk 4 or fragment, or an analogue, derivative, variant or functional mimetic thereof, is immobilised whereupon the other is applied in the presence of the agents under test. In a scintillation proximetry assay a biotinylated protein fragment is bound to streptavidin coated scintillant—impregnated beads (produced by Amersham). Binding of radiolabelled peptide is then measured by determination of radioactivity induced scintillation as the radioactive peptide binds to the immobilized fragment. Agents which intercept this are thus inhibitors of the interaction.

In one general aspect, the present invention provides an assay method for a substance with ability to disrupt interaction or binding between p21 and cyclin D1 and/or Cdk4, the method including:
(a) bringing into contact a substance according to the invention including a peptide fragment of p21 or a derivative, variant or analogue thereof as disclosed, a substance including the relevant fragment of cyclin D1 and/or Cdk4 or a variant, derivative or analogue thereof, and a test compound, under conditions wherein, in the absence of the test compound being an inhibitor of interaction or binding of said substances, said substances interact or bind; and
(b) determining interaction or binding between said substances.

A test compound which disrupts, reduces, interferes with or wholly or partially abolishes binding or interaction between said substances (e.g. including a p21 fragment and including a cyclin D1 and/or Cdk 4 fragment), and which may modulate Cdk4 activity, may thus be identified.

Another general aspect of the present invention provides an assay method for a substance able to bind the relevant region of p21 as the case may be, the method including:
(a) bringing into contact a substance which includes a peptide fragment of p21 which interacts with cyclin D1 and/or Cdk 4 as disclosed, or a variant, derivative or analogue thereof as disclosed, and a test compound; and
(b) determining.binding between said substance and the test compound.

A test compound found to bind to the relevant portion of p21 may be tested for ability to disrupt p21 interaction or binding with cyclin D1 and/or Cdk 4 and/or ability to affect Cdk4 activity or other activity mediated by p21 as discussed already above.

Performance of an assay method according to the present invention may be followed by isolation and/or manufacture and/or use of a compound, substance or molecule which tests positive for ability to interfere with interaction between p21 and cyclin D1 and/or Cdk4 and/or inhibit p21-mediated Cdk4 activity.

The precise format of an assay of the invention may be varied by those of skill in the art using routine skill and knowledge. For example, interaction between substances may be studied in vitro by labelling one with a detectable label and bringing it into contact with the other which has been immobilised on a solid support. Suitable detectable labels, especially for petidyl substances include $^{35}S$-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay The in vivo assay may be performed in a cell line such as a yeast strain or mammalian cell line in which the relevant polypeptides or peptides are expressed from one or more vectors introduced into the cell.

The ability of a test compound to disrupt interaction or binding between p21 and cyclin D1 and/or Cdk4 may be determined using a so-called two-hybrid assay.

For example, a polypeptide or peptide containing a fragment of p21 or cyclin D1/Cdk4 as the case may be, or a peptidyl analogue or variant thereof as disclosed, may be fused to a DNA binding domain such as that of the yeast transcription factor GAL 4. The GAL 4 transcription factor includes two functional domains. These domains are the DNA binding domain (GAL4DBD) and the GAL4 transcriptional activation domain (GAL4TAD) By fusing one polypeptide or peptide to one of those domains and another polypeptide or peptide to the respective counterpart, a functional GAL 4 transcription factor is restored only when two polypeptides or peptides of interest interact. Thus, interaction of the polypeptides or peptides may be measured by the use of a reporter gene probably linked to a GAL 4 DNA binding site which is capable of activating transcription of said reporter gene. This assay format is described by Fields and Song, 1989, Nature 340; 245–246. This type of assay format can be used in both mammalian cells and in yeast. Other combinations of DNA binding domain and transcriptional activation domain are available in the art and may be preferred, such as the LexA DNA binding domain and the VP60 transcriptional activation domain.

To take a Lex/VP60 two hybrid screen by way of example for the purpose of illustration, yeast or mammalian cells may be transformed with a reporter gene construction which expresses a selective marker protein (e.g. encoding β-galactosidase or luciferase). The promoter of that gene is designed such that it contains binding site for the LexA DNA-binding protein. Gene expression from that plasmid is usually very low. Two more expression vectors may be transformed into the yeast containing the selectable marker expression plasmid, one containing the coding sequence for the full length LexA gene linked to a multiple cloning site. This multiple cloning site is used to clone a gene of interest, i.e. encoding a p21 or cyclinD1/Cdk4 polypeptide or peptide in accordance with the present invention, in frame on to the LexA coding region. The second expression vector then contains the activation domain of the herpes simplex transactivator VP16 fused to a test peptide sequence or more preferably a library of sequences encoding peptides with diverse e.g. random sequences. Those two plasmids facilitate expression from the reporter construct containing the selectable marker only when the LexA fusion construct interacts with a polypeptide or peptide sequence derived from the peptide library.

A modification of this when looking for peptides or other substances which interfere with interaction between a p21 polypeptide or peptide and an cyclin D1/Cdk 4 polypeptide or peptide, employs the p21 or cyclin D1/Cdk4 polypeptide or peptide as a fusion with the LexA DNA binding domain, and the counterpart cyclin D1/Cdk4 or p21 polypeptide or peptide as a fusion with VP60, and involves a third expression cassette, which may be on a separate expression vector, from which a peptide or a library of peptides of diverse and/or random sequence may be expressed. A reduction in reporter gene expression (e.g. in the case of β-galactosidase a weakening of the blue colour) results from the presence of a peptide which disrupts the p21/cyclinD1 and/or Cdk4 interaction, which interaction is required for transcriptional activation of the β-galactosidase gene. Where a test substance is not peptidyl and may not be expressed from encoding nucleic acid within a said third expression cassette, a similar system may be employed with the test substance supplied exogenously.

As noted, instead of using LexA and VP60, other similar combinations of proteins which together form a functional transcriptional activator may be used, such as the GAL4 DNA binding domain and the GAL4 transcriptional activation domain.

When performing a two hybrid assay to look for substances which interfere with the interaction between two polypeptides or peptides it may be preferred to use mammalian cells instead of yeast cells. The same principles apply and appropriate methods are well known to those skilled in the art.

The amount of test substance or compound which may be added to an assay of the invention will normally be determined by trial and error depending upon the type of compound used. Typically, from about 0.01 to 100 nM concentrations of putative inhibitor compound may be used, for example from 0.1 to 10 nM. Greater concentrations may be used when a peptide is the test substance.

Compounds which may be used may be natural or synthetic chemical compounds used in drug screening programmes. Extracts of plants which contain several characterised or uncharacterised components may also be used.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies may also be used in purifying and/or isolating a polypeptide or peptide according to the present invention, for instance following production of the polypeptide or peptide by expression from encoding nucleic acid therefor. Antibodies may be useful in a therapeutic context (which may include prophylaxis) to disrupt p21/cyclin D1/Cdk4 interaction with a view to inhibiting Cdk4 activity and so cellular proliferation. Antibodies can for instance be microinjected into cells, e.g. at a tumour site.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect Cdk4 activity has therapeutic potential in anti-tumour treatment, and may be used in combination with any other anti-tumour compound. In such a case, the assay of the invention, when conducted in vivo, need not measure the degree of inhibition of binding or of modulation of Cdk4 activity caused by the compound being tested. Instead the effect on tumorigenicity and/or cell viability may be measured. It may be that such a modified assay is run in parallel with or subsequent to the main assay of the invention in order to confirm that any effect on tumorigenicity or and/or cell viability is as a result of the inhibition of binding or interaction between p21 and cyclin D1/Cdk 4 caused by said inhibitor compound and not merely a general toxic effect.

Following identification of a substance or agent which modulates or affects Cdk4 activity, the substance or agent may be investigated further. Furthermore, it may be manufactured and/or used in preparation, i.e. manufacture or formulation, of a composition such as a medicament, pharmaceutical composition or drug. These may be administered to individuals.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the binding between p21 and cyclin D1/Cdk4. Examples of such analogues include chemical compounds which are modelled to resemble the three dimensional structure of the p21 or cyclin D1/Ckd4 domain in the contact area, and in particular the arrangement of the key amino acid residues identified above as they appear in human p21.

In a further aspect, the present invention provides the use of the above substances in methods of designing or screening for mimetics of the-substances.

Accordingly, the present invention provides a method of designing mimetics of p21$^{WAF1}$ having the biological activity of Cdk4 binding or inhibition, the activity of allosteric inhibition of Cdk4 and/or the activity of cyclin D1 binding, said method comprising:

(i) analysing a substance having the biological activity to determine the amino acid residues essential and important for the activity to define a pharmacophore; and, (ii) modelling the pharmacophore to design and/or screen candidate mimetics having the biological activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

The present invention further provides the use of a peptide which includes a sequence as disclosed, or a derivative, active portion, analogue, variant or mimetic, thereof able to bind Cdk4 and/or inhibit Cdk4 activity, in screening for a substance able to bind Cdk4 and/or inhibit Cdk4 activity.

Generally, an inhibitor according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an inhibitor compound as disclosed, one or more other molecules of therapeutic use, such as an anti-tumor agent.

The present invention extends in various aspects not only to a substance identified as a modulator of p21 and cyclin D1/Ckd4 interaction and/or Cdk4-mediated RB phosphorylation or other substrates of Cdk4 or other p21-mediated activity, property or pathway in accordance with what is disclosed herein, but also a pharmaceutical composition, medicament, drug or other composition comprising such a substance, a method comprising administration of such a composition to a patient, e.g. for anti-tumour or other anti-proliferative treatment, which may include preventative treatment, use of such a substance in manufacture of a composition for administration, e.g. for anti-tumour or other anti-proliferative treatment, and a method of making a pharmaceutical composition comprising admixing such a substance with a pharmaceutically acceptable excipient, vehicle or carrier, and optionally other ingredients.

A substance according to the present invention such as an inhibitor of p21 and cyclin D1 and/or Cdk4 interaction or binding may be provided for use in a method of treatment of the human or animal body by therapy which affects Cdk 4 activity or other p21-mediated activity in cells, e.g. tumour cells.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, Thus the invention further provides a method of modulating Cdk4 activity, or other p21-mediated activity in a cell, which includes administering an agent which inhibits or blocks the binding of p21 to cyclin D1 and/or Cdk4 protein, such a method being useful in treatment of cancer or other diseases or disorders including malignancies where inhibition of cellular growth and/or proliferation is desirable.

The invention further provides a method of treating tumours which includes administering to a patient an agent which interferes with the binding of p21 to cyclin D1 and/or Cdk4.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A composition may be administered alone or in combination with other treatments, either simultaneously or sequentially dependent upon the condition to be treated.

antioxidants and/or other additives may be included, as required.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, eg in a viral vector (a variant of the VDEPT technique—see below). The vector may targeted to the specific cells to be treated, or it may contain regulatory elements which are switched on more or less selectively by the target cells.

The agent may be administered in a precursor form, for conversion to the active form by an activating agent produced in, or targeted to, the cells to be treated. This type of approach is sometimes known as ADEPT or VDEPT, the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated, such as cancer, virus infection or any other condition in which a p21-mediated effect is desirable.

Nucleic acid according to the present invention, encoding a polypeptide or peptide able to interfere with p21 and cyclin D1 and/or Cdk 4 interaction or binding and/or induce or modulate Cdk4 activity or other p21-mediated cellular pathway or function, may be used in methods of gene therapy, for instance in treatment of individuals with the aim of preventing or curing (wholly or partially) a tumour e.g. in cancer, or other disorder involving loss of proper regulation of the cell-cycle and/or cell growth, or other disorder in which specific cell death is desirable, such as in certain viral infections.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to interfere with the interaction of the relevant polypeptide, peptide or other substance as disclosed herein, or a nucleic acid molecule encoding a peptidyl such molecule, may be provided in a kit, e.g. sealed in a suitable container which protects its contents from the external environment. Such a kit may include instructions for use.

Various further aspects and embodiments of the present invention will be apparent to those skilled in the art in view of the present disclosure. Certain aspects and embodiments of the invention will now be illustrated by way of example and with reference to the following figures:

FIG. 1. The Ability of Peptides from p21$^{WAF1}$ to Interact with Cdk4 and Cyclin D1.

FIG. 1a: a list of the peptides 1–11 based on the sequence of p21$^{WAF1}$.

FIG. 1b: The p21$^{WAF1}$ peptides were bound to streptavidin-agarose beads and added to reticulocyte lysates containing either Cdk4 or cyclin D1 labelled with [$^{35}$S] methionine. After extensive washing bound proteins were analysed using SDS-PAGE followed by autoradiography. The bands were quantified using a Bio-Imager and Whole Band Analysis Software (Millipore). The results are representative of 3 such experiments. "x" indicates beads without peptide. Peptides 1–11 correspond with SEQ ID NO:1 to SEQ ID NO:11 respectively.

Figure 2:
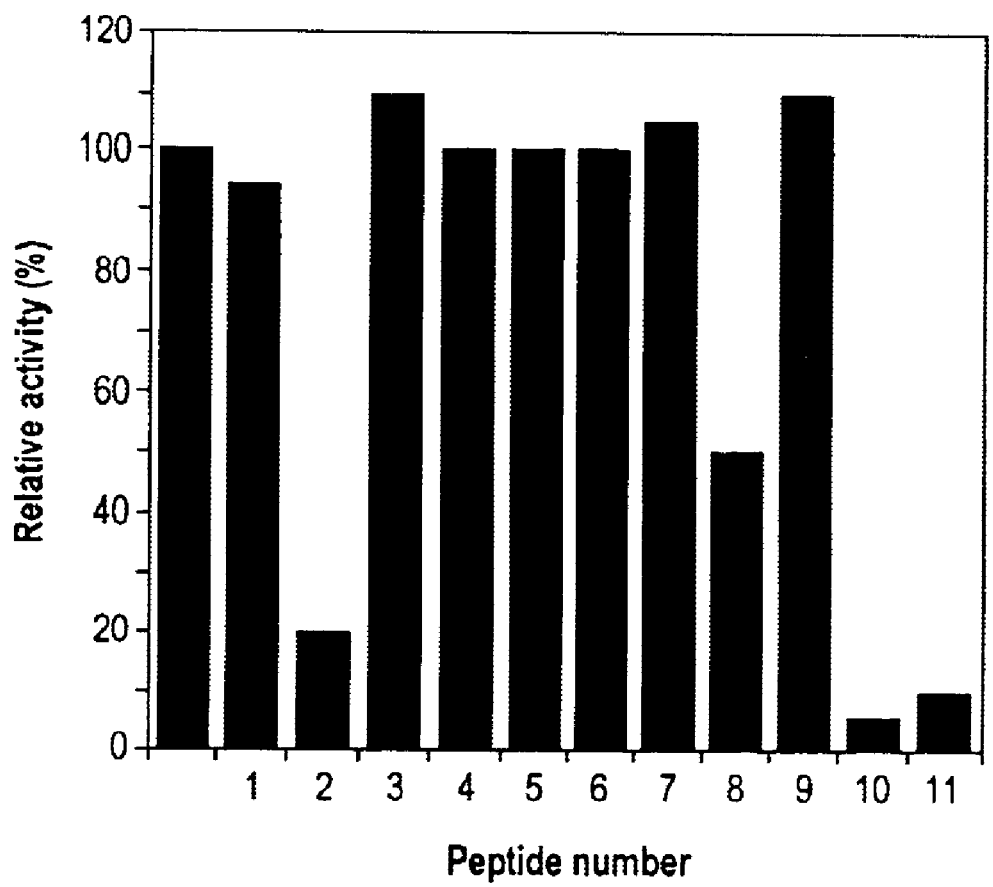

FIG. 2. Addition of p21$^{WAF1}$ Based Peptides to Cyclin D1-Cdk4 Phosphorylation Assays.

Cyclin D1-Cdk4 assays were carried out in vitro using lysates from Sf9 insect cell following co-infection with Cdk4 and cyclin D1 baculovirus constructs and GST-Rb as the substrate. p21$^{WAF1}$ peptides were added to the assays at a concentration of 17 µM and the effect on Cdk4 activity was assessed by SDS-PAGE and autoradiography. The figure shows quantification of the autoradiograph using bio-imaging, relative binding is expressed in terms of Cdk4 activity in the absence of peptide. The data are representative of 4 experiments. "x" indicates no addition of peptide.

Figure 3:
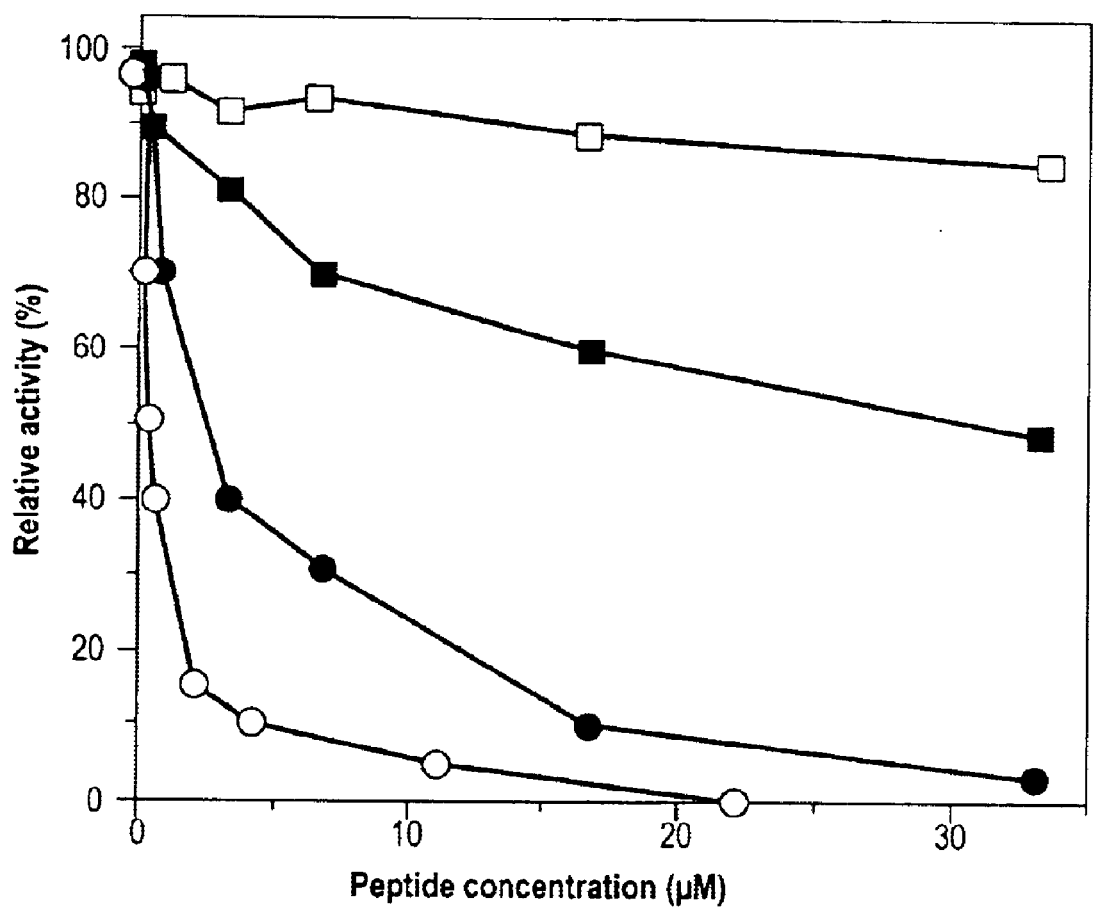

FIG. 3. Quantification of Peptide Inhibition.

Peptides 4, 8, 2 and 10 were added to cyclin D1-Cdk4 assays at various concentrations between 0.01–34 µM. The figure gives a plot of activity (%) relative to Cdk4 activity measured in the absence of peptide against peptide concentration and the $I_{0.5}$ for each peptide. The data represent the mean of 3 experiments.

Figure 4:
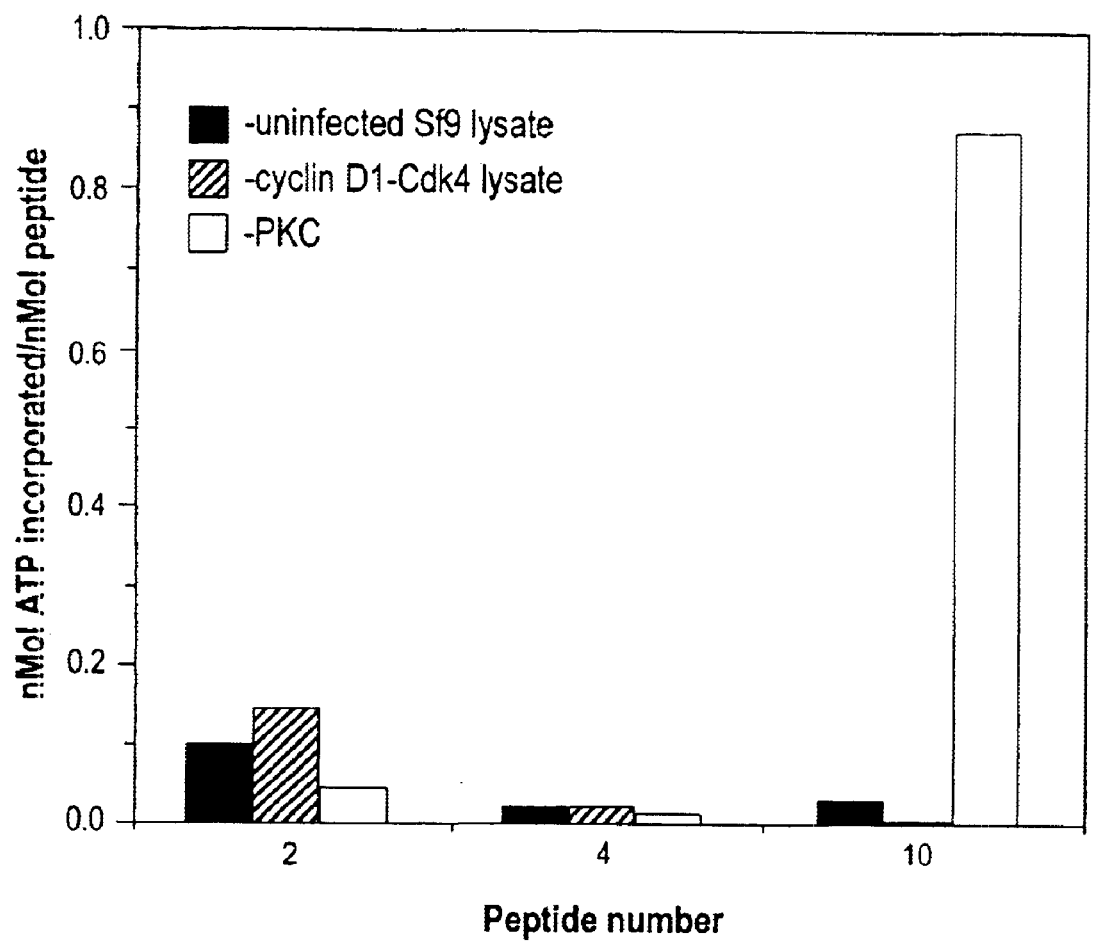

FIG. 4. Peptides 2 or 10 are Not Substrates for Cyclin D1-Cdk4.

The figure shows the results of phosphorylation assays using peptides 2, 4 & 10.

FIG. 5. Size Scan of Peptide 10.

The figure shows the sequences of a series of peptides based on peptide 10 designed to find the minimal inhibitory domain. The boxed residues represent the minimal inhibitory domain. The peptides ware added to cyclin D1-Cdk4 assays and analysed by SDS-PAGE and autoradiography. (Peptide a corresponds with SEQ ID NO:16; peptide b corresponds with SEQ ID NO:17; peptide c corresponds with SEQ ID NO:18; peptide d corresponds with SEQ ID NO:19; peptide e corresponds with SEQ ID NO:20; peptide 10 corresponds with SEQ ID NO:10; peptide f corresponds with SEQ ID NO:21: and pentide g corresponds with SEQ ID NO:22.

FIG. 6. Alanine Scan Mutations of Peptide 10.

In order to pinpoint residues that were critical for the inhibition of Cdk4 by peptide 10 a series of point mutations were constructed in which each residue was sequentially changed to alanine. The peptides were added to cyclin D1-Cdk4 assays and the results were analysed by SDS-PAGE and autoradiography then quantified using a Bio-Imager. The results are expressed relative to Cdk4 activity in the absence of peptide and are representative of 3 experiments. Having identified the critical residues we then synthesised an untagged eight amino acid peptide which contained the R, L and F (KRRLIFS)(SEQ ID NO:23) and determined the phosphorylation of GST-Rb by cyclin D1-Cdk4 in the presence of increasing concentrations of this truncated peptide.

Figure 7:
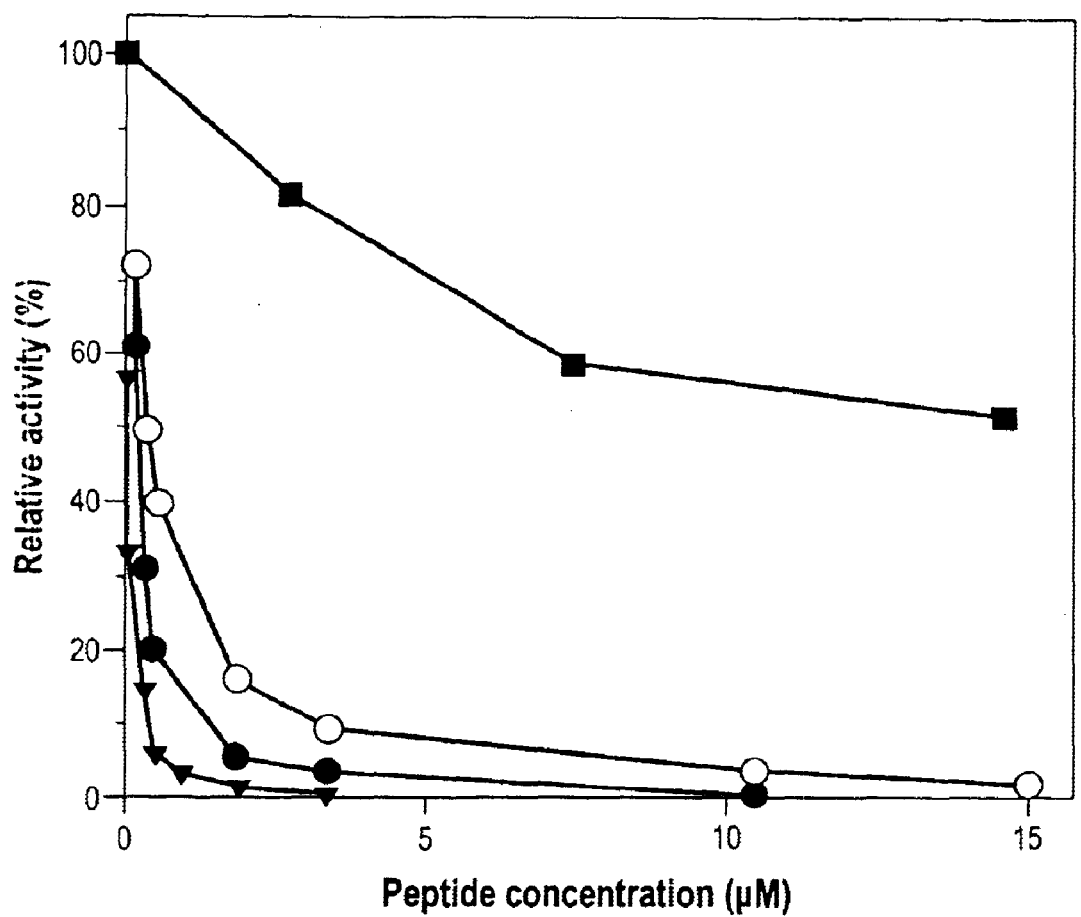

FIG. 7. Comparison of Inhibitory Peptides with Full Length p21$^{WAF1}$ Protein.

This shows concentration curves for peptide 10, D to A mutant peptide 10, a p16INK4 derived peptide (Fahraeus et al., 1996) and full length his-p21$^{WAF1}$ determined using the cyclin D1-Cdk4 assay analysed by SDS-PAGE, autoradiography and bio-imaging and for the $I_{0.5}$ of each inhibitor. The results are the mean of 3 such experiments.

Figure 8:
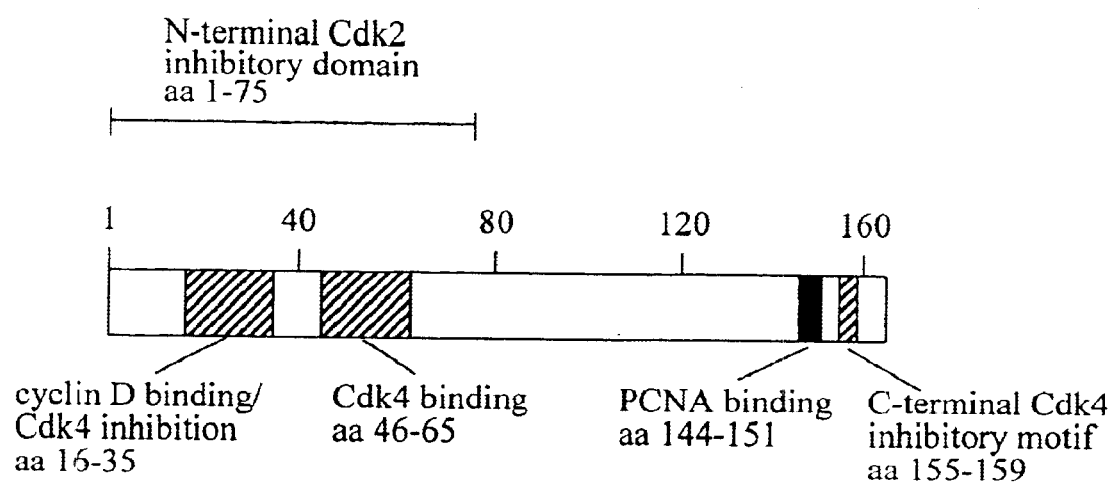

FIG. 8. Binding and Inhibitory Domains of p21$^{WAF1}$.

The hatched residues show the regions of p21$^{WAF1}$ identified in this study as being important for cyclin D1 and Cdk4 binding, and Cdk4 inhibition in the N-terminal domain, as well as a novel inhibitory domain in the C-terminus of p21$^{WAF1}$. The residues found to be important for the interaction of p21$^{WAF1}$ with PCNA (Warbrick et al., 1995) are shown in black. In addition, the smallest portion of p21$^{WAF1}$ that was found to inhibit CDK activity in vitro (Luo et al., 1995) prior to the present study is indicated.

FIG. 9. Introduction of p21$^{WAF1}$ based peptides into cells

Figures 9A, 9B, 9C:
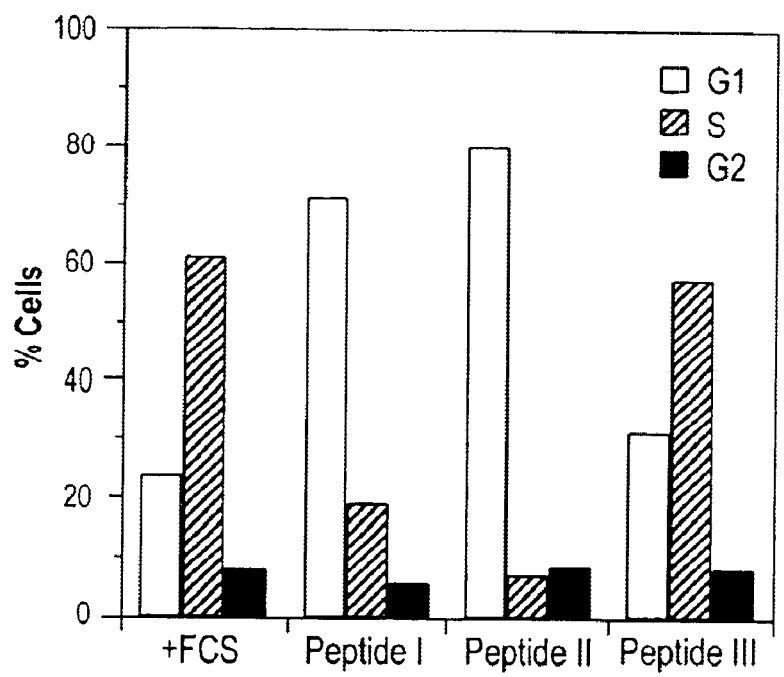

A series of synthetic peptides based on the sequence of peptide 10 (Peptides I, II and III, shown in FIG. 9a) were synthesised with carrier peptide (shaded sequences). The underlined residue in peptide-I is the M to A mutation which prevents PCNA binding. The peptides were added to proliferating HaCaT cells, grown in DMEM plus 10% FCS. The cells were incubated for 24 hours pulse labelled during with 15 μM BrdU, fixed and then analysed by FACS. The $G_1$-, S- and $G_2$-phase distributions for untreated cells, Peptide-I at 25 μM, Peptide-II at 50 μM and Peptide-III at 25 μM, were determined. FIG. 9b shows the data represented as the % of cells in each phase compared to the total number of cells counted. The results of similar experiments using MCF7 and MRCS cells are shown in FIG. 9c, which shows the percentage of cells in each phase of the cell cycle in the absence and presence of peptide I.

In a separate experiment DMEM+10% FCS alone or DMEM+10% FCS containing either 25 μM Peptide-I or 50 μM Peptide-II, was added to HaCaT cells than had been starved for 72 hours. Samples were taken at the times shown and analysed by SDS-PAGE/Western blot stained for pRb. pRb represents hypophosphorylated Rb protein and pRb* refers to hyperphosphorylated Rb protein. It should be pointed out that equal amounts of total protein were loaded per lane and that the antibody appears to preferentially recognise phosphorylated forms of the Rb protein. Peptide I corresponds with SEQ ID NO:24; peptide II corresponds with SEQ ID NO:25; and peptide III corresponds with SEQ ID NO:26.

Figure 10:
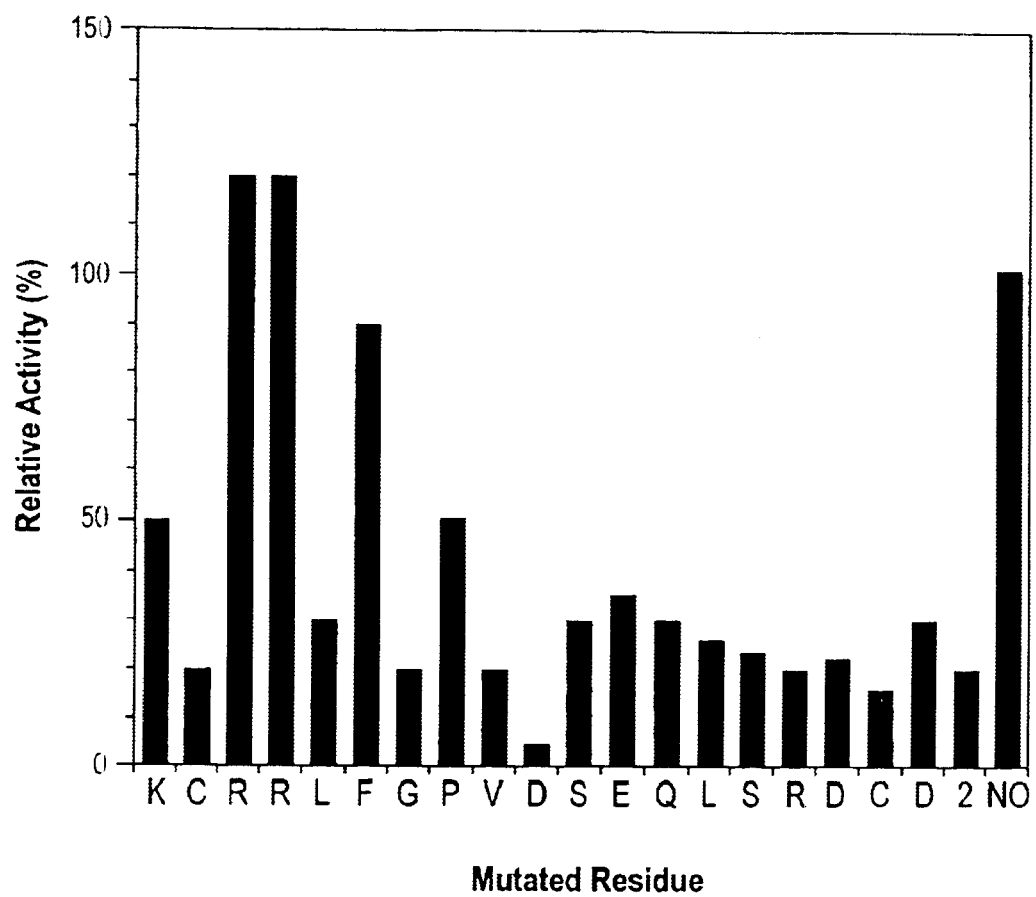

FIG. 10. Inhibition of cyclin-Cdk4 activity using derivatives of peptide 2.

The figure shows the degree of inhibition of cyclin D1-Cdk4 activity using pRb as a substrate, by peptide 2 (2 on the figure) and alanine scan mutations of the peptide (each residue being sequentially mutated to alanine). Activity is given relative to uninhibited activity. (No is short for no added peptide.) Peptides were present at a concentration of 10 μM. A similar pattern is seen when binding of peptide 2 mutants to cyclin D1 expressed in reticulocyte lysates.

Important residues for the binding and inhibition are the two arginine residues (R) and the phenylalanine (F) with the lysine (K) and proline (P) also contributing. This is different from residues identified as being critical for interaction of full length protein with cyclin D1, as these studies pick out the LFG motif as being most important for activity.

EXPERIMENTAL PROCEDURES

Peptides

All peptides were synthesised by Chiron Mimotopes, Peptide Systems (Clayton, Australia). Each peptide had a Biotin-SGSG spacer at the C-terminus and a free N-terminus. The peptides were dissolved in DMSO at approximately 5 mg/ml and we then determined their concentration precisely by amino acid analysis (Smythe et al., 1988). In addition the purity of the peptides was estimated using mass spectrometry. Positive ion electrospray mass spectrometry was performed on a triple-quadruple mass spectrometer (V. G. Quattro) in (50/50/0.1) water/acetonitrile/formic acid.

Proteins

Cyclins and CDKs—Cdk4 and cyclin D1, Cdk2 and cyclin E and Cdc2 and cyclin B were co-expressed in Sf9 insect cells infected with the appropriate baculovirus constructs. The cells were harvested two days after infection by low speed centrifugation and the pellet was lysed in an equal volume of 10 mM Hepes, pH 7.4 containing: 10 mM NaCl, 1 mM EDTA, and 0.1 mM phenylmethane sulphonyl fluoride, 2 mM DTT and centrifuged at 14000×g for 15 min. The supernatant was removed, aliquoted and immediately frozen in liquid nitrogen. Thawed lysate was used only once and was never refrozen. Labelled Cdk4 and cyclin D1 were produced by translation in the presence of [$^{35}$S] methionine using a rabbit reticulocyte lysate in vitro translation kit (Promega).

His-tacqed p21$^{WAF1}$—Human p21$^{WAF1}$ was expressed in E.coli using a PET expression vector. The soluble p21$^{WAF1}$ protein fraction was purified using a nickel chelating column, following the manufacturers instructions (Pharmacia). The eluted protein peak was dialysed against 25 mM Hepes, pH 7.4, containing: 0.1 mM EDTA, 1 mM benzamidine, 0.01% Triton X-100, and 0.1 mM phenylmethane sulphonyl fluoride, concentrated and applied to a Superose 12 gel-filtration column (Phamacia) equilibrated in the above buffer. Fractions containing p21$^{WAF1}$ were detected by Western blot using the p21$^{WAF1}$ specific monoclonal antibody Ab-1 (oncogene Sciences), concentrated to 200 μg/ml and stored at −70° C.

GST-Rb—An E. coli expression construct containing the hyperphosphorylation domain of pRb (amino acids 773–924) was purified on a glutathione-Sepharose column according to the manufacturers instructions (Pharmacia).

Peptide Precipitation of cdk4 and Cyclin D1

A amino acid peptide library, that spanned the entire sequence of p21$^{WAF1}$ (FIG. 1), was screened for Cdk4/cyclin D1 interacting peptides. Peptide (1.5 μg) was diluted in 100 μl of PBS and incubated with 10 μl of packed streptavidin-agarose beads (Sigma) for 1 h at room temperature. Unbound peptide was removed by extensive washing with PBS and the beads, plus bound peptide, were incubated for 1 h at 4° C. with reticulocyte lysate containing either Cdk4 or cyclin D1 labelled with [$^{35}$S] methionine. The beads were washed three times with 1.25×PBS containing 0.2% Triton X-100 and boiled in the presence of 0.125 M Tris-HCl, pH 6.8 containing: 4% (w/v) SDS, 20% (v/v) glycerol and 200 mM DTT. The bound protein was analysed by SDS-PAGE followed by auto-radiography and quantification of the $^{35}$S-labelled protein using a Bio-Imager and Whole Band Analysis Software (Millipore).

Enzyme Assays

Phosphorylation of GST-Rb—Cdk4 activity was measured using the cyclin D1-Cdk4 containing insect cell lysate described above. Extract (1 μl) was added to a final reaction volume of 10 μl, containing: 50 mM Hepes, pH 7.4, 10 mM MgCl2, 2.5 mM EGTA, 1 mM DTT, 10 mM β-glycerophosphate, 1 mM NaF, 10 mM PKI, 50 μM ATP containing [$^{32}$P] ATP (1000 cpm/pMol) and 0.5 μg GST-Rb. The assays were started by the addition of the GST-Rb substrate, incubated at 30° C. for 10 min (the incorporation of $^{32}$P into GST-Rb was linear over 15–20 min) and terminated by adding SDS-PAGE sample buffer and heating at 95° C. for 4 min. The samples were analysed by SDS-PAGE on 12% gels followed by auto-radiography and quantification using a Bio-Imager.

Peptide Phosphorylation

The biotinylated peptides (1 μg) were incubated for 30 min at 30° C. in a final volume of 20 μl containing: 50 mM Hepes, pH 7.4, 10 mM MgCl$_2$, 2.5 mM EGTA, 1 mM DTT, 10 mM β-glycerophosphate, 1 mM NaF, 10 mM PKI, 50 μM ATP containing [$^{32}$P]ATP (6000 cpm/pMol) and either 1 μl of cyclin D1-Cdk4 insect cell lysate, 1 μl of uninfected insect cell lysate or 0.02 mU of protein kinase C plus 0.5 mM CaCl$_2$, 100 mg/ml phosphatidyl serine and 20 mg/ml diacylglycerol. The reactions were stopped by heating at 60° C. for 5 min and streptavidin agarose beads were added (10 μl packed cell volume washed with 3×PBS) and incubated with shaking at 4° C. for 30 min. The beads were washed extensively with PBS containing 3% (v/v) Tween-20 and the incorporation of radioactivity into the peptides was determined by Cerenkov counting.

Cell Cycle Measurements

Carrier linked peptides were designed for delivery into proliferating HaCaT cells (see FIG. 9). Cells were seeded on 30mm culture plates and grown to 50% confluency in Dulbecco's modified Eagle's medium (DMEM) supplemented with 10% (v/v) foetal calf serum (FCS). Peptides were added to the medium and the cells were incubated for 24 hours. During the last 30 minutes of the incubation the cells were pulse labelled in the presence of 15 $\mu$M BrdU. The cells were trypsinised, fixed in absolute alcohol and prepared for FACS analysis using a single laser flow cytometer (Becton-Dickinson, FACScan) as previously described (Renzing et al, 1996).

pRb Phosphorylation in HaCaT Cells

HaCaT cells were seeded on 30 mm culture plates at 25% confluency in DMEM with 10% FCS. The FCS was withdrawn after 24 hours and the cells were starved for 72 hours. At the end of this period the medium was supplemented with 10% FCS and carrier linked peptides. Samples were taken over a 24 hour time course and the cells were lysed in RIPA buffer (50 mM Tris-HCl, pH 8.0, containing 150 mM NaCl, 1.0% (v/v) NP-40, 0.5% (w/v) DOC, 0.1% (w/v) SDS, 1 mM PMSF, 0.1 mg/ml aprotinin and 0.5 mg/ml leupeptin) for 30 minutes at 4° C. The phosphorylation statues of pRb was determined by Western blot analysis, as previously described (Fåhraeus et al, 1996) except that the blot was probed with a pRb polyclonal antibody (C-15, Santa Cruz).

Results

Peptide-Binding Assay for Cyclin D1 and Cdk4

Using a series of synthetic peptides that span the entire sequence of p21$^{WAF1}$ (FIG. 1), we determined whether these peptides could mimic full length p21$^{WAF1}$ protein by forming a stable complex with either cyclin D1 or Cdk4. If peptide-binding mimetics of p21$^{WAF1}$ protein could be identified, then this would assist in identifying the minimal binding motif of p21$^{WAF1}$ protein required for cyclin D1-Cdk4 holoenzyme inhibition and whether p21$^{WAF1}$ was targeting the cyclin or the kinase subunit. This would also define a system for using small peptides to study p21$^{WAF1}$ protein reaction mechanism and to design mimetic drugs.

The peptide-binding assay involved quantifying the amount of $^{35}$S-labelled cyclin D1 or Cdk4 which bound specifically to biotinylated peptides that were captured on streptavidin coated agarose beads. The peptide-coated beads were added to extracts containing either $^{35}$S-labelled cyclin D1 or Cdk4 translated in vitro, the beads were washed extensively to remove unbound protein, and the bound cyclin D1 or Cdk4 was quantified by SDS-PAGE followed by auto-radiography and bio-imaging. This is referred to below as a peptide precipitation assay and has been used previously to demonstrate evolutionary conservation of p21$^{WAF1}$ binding to PCNA (Ball and Lane, 1996).

A Small Peptide Derived from Amino Acids 46–65 in the N-Terminal Domain of p21$^{WAF1}$ Binds Directly to Cdk4

Using the peptide-precipitation assay, peptide 4 (from the N-terminal domain of p21$^{WAF1}$) bound specifically to Cdk4, but not to cyclin D1 (FIG. 1). This interaction is physiologically important, since the CDK interacting domain of the p21$^{WAF1}$ protein has previously been proposed to localise to the N-terminal domain of the molecule (Chen et al.,1995; Harper et al., 1995; Luo et al., 1995). More specifically, deletions (Nakanishi et al., 1995a) or mutations (Goubin and Ducommun, 1995) in the region of amino acids 45–71 compromise the ability of full length p21WAF1 to interact with Cdk2. Whether this loss of p21WAF1 binding function is due to, (i) mutation/deletion of residues directly involved in CDK binding, or (ii) mutations/deletion induced conformational alterations in p21$^{WAF1}$ that prevent stable binding to CDK, has not been demonstrated. Here we show unequivocally that residues 46–65 are directly involved in the binding of p21$^{WAF1}$ to Cdk4 and that alone they are capable of forming a stable complex with Cdk4, in the absence of cyclin D1. Thus, providing direct evidence that the N-terminus of p21$^{WAF1}$ does contain a kinase binding domain.

A Small Peptide Derived from Amino Acids 16–35 in the N-Terminus of p21$^{WAF1}$ Binds Directly to Cyclin D1

We were also able to define a second and distinct N-terminal interaction site on the p21$^{WAF1}$ protein; in this case a region of p21$^{WAF1}$ which is capable of binding to cyclin D1, but not to Cdk4 (FIG. 1). Peptide 2 comprises amino acids 16–35 of p21$^{WAF1}$ and lies within the Eminimum region required for DNA synthesis inhibition in vivo, which is located between residues 17–71 (Nakanishi et al., 1995a). Our results might explain an apparent contradiction encountered by Nakanishi et al. (1995a) who found that N-terminal mutations in p21$^{WAF1}$ protein which are outside the CDK interacting domain, although insufficient to prevent binding to the kinase, were sufficient to prevent p21$^{WAF1}$ from acting as a growth suppressor when transfected into proliferating cells. Specifically, the direct peptide binding data (FIG. 1) leads us to suggest that an N-terminal motif in the p21$^{WAF1}$ protein, that mediates cyclin D1 binding, could be an essential step in the mechanism through which p21$^{WAF1}$ protein functions as a growth suppressor.

A Novel Cyclin D1-Cdk4 Binding Motif Resides in the C-Terminus of the p21$^{WAF1}$ Protein The specificity of the peptide-precipitation assay in defining the domain of p21$^{WAF1}$ protein required for binding to either the cyclin D1 or Cdk4 (FIG. 1), indicated that using peptides to study potential interactions between p21$^{WAF1}$ and cyclin-CDK complexes would prove to be very informative. We were intrigued however, by the finding that peptides from the C-terminus of the p21$^{WAF1}$ protein (peptides 10 and 11) could form stable complexes with both Cdk4 and cyclin D1 (FIG. 1), as peptide 10 is equivalent to the p21PBP peptide described by Warbrick et al. (1995) as representing the region of p21$^{WAF1}$ which binds to the replication/repair protein PCNA. We can not rule out the possibility that endogenous cyclin or CDK present in the reticulocyte lysate could bind to the labelled human protein forming a bridge to the peptide. However, as peptide 2 and peptide 4 precipitate either cyclin D1 or Cdk4, respectively, this seems unlikely. These results suggest that the p21$^{WAF1}$ protein may interact with both PCNA and cyclin-CDK complexes through the same binding motif. Peptide 11 however, binds to both Cdk4 and cyclin D1 but not to PCNA (FIG. 1) (Warbrick et al., 1995; Ball and Lane, 1996); uncoupling the PCNA binding site from the cyclin/CDK binding motif in the C-terminus of p21$^{WAF1}$.

Given that we had identified three distinct motifs from the p21$^{WAF1}$ protein which bind specifically to cyclin D1 and/or Cdk4, we then examined whether they mimicked p$_p$21$^{WAF1}$ protein by inhibiting kinase activity.

The Cyclin D1 Binding Peptide from the N-Terminal Domain of p21$^{WAF1}$ and the Cyclin/CDK Binding Peptide from the C-Terminus of p21$^{WAF1}$ Inhibits the Activity of Cdk4

In order to determine if any of the p21$^{WAF1}$ peptides possessed

Cdk4 inhibitory activity we tested, independently, their ability to prevent pRb phosphorylation during cyclin D1-Cdk4 assays in vitro (FIG. 2). Peptides 2, 8,10, and 11 inhibited cyclin D1-Cdk4 activity when added to the assay at 17 $\mu$M, whereas buffer alone and the remaining peptides had no dramatic affect on Cdk4 activity. The cyclin D1 binding peptide (peptide 2) inhibited the kinase activity by approximately 80% and peptides 10 and 11, which bound both Cdk4 and cyclin D1, completely inhibited enzyme activity at this concentration. Thus, there is a correlation between the ability of the peptides to bind to Cdk4 and/or cyclin D1 and to inhibit Cdk 4 kinase activity.

However, this correlation breaks down in the case of kinase-binding peptide 4. This peptide maps to the CDK interaction site (FIG. B; Goubin and Ducommun, 1995; Nakanishi et al., 1995a) and there has been speculation that a peptide from this domain, capable of interacting with CDK, would mimic full-length p21$^{WAF1}$ inhibitory activity, and would therefore provide a model for the design of novel. molecules that could arrest cell cycle progression by inhibiting the G1 cyclin-CDKs. Although of high affinity for Cdk4, peptide 4 had no inhibitory activity when added to cyclin D1-Cdk4 assays at concentrations of up to 35 $\mu$M. Our data from both p21$^{WAF1}$-peptide binding data and inhibitory properties, therefore pinpoints two novel small domains of the p21$^{WAF1}$ protein as potential candidates for small molecular weight mimetics; an N-terminal motif from amino acids 16–35 (peptide 2) and a C-terminal motif from amino acids 141–160 (peptide 10).

It is thus possible that peptide 4 could block p21 binding, preventing its activity as an inhibitor. Thus cells treated with peptide 4 may be expected to continue to proliferate even in the presence of competing signals which would normally mediate cell cycle arrest or apoptosis. Thus peptide 4 may be used to reversibly immortalise cells, by supplying to the peptide to the cells. This provides a further tool in investigating the cellular mechanismns for control of the cell cycle and may also be useful in combatting cell loss in conditions associated with loss of cells, such as in AIDS or degenerative conditions including MS, dementia, or in muscle degenerative conditions such as munscular dystropy (MD) including Duchenne MD.

The C-Terminal p21$^{WAF1}$ Peptide is a More Potent Inhibitor of Cdk4 Kinase Activity than the N-Terminal Cyclin D1-Binding Peptide We carried out, more detailed studies to determine the $I_{0.5}$ for peptides 2, 8, and 10, using peptide 4 as a negative control (FIG. 3). We found that peptide 10 (and peptide 11; data not shown) was a potent inhibitor of Cdk4 activity with an $I_{0.5}$ of 0.1 $\mu$M, peptide 2, was also a good inhibitor with an $I_{0.5}$ of 2 $\mu$M Peptide 8 gave only weak inhibition and relatively high concentrations of peptide were required to approach 50% inhibition. These data support the possibility of using peptide 2 or peptide 10 to mimic the CDK inhibitory activity of the full length p21$^{WAF1}$ protein.

p21$^{WAF1}$ Protein and Inhibitory Peptides Compete for the Same Binding Site on Cdk4 Kinase In order to determine if the Cdk4 inhibitory peptides, 2 and 10, were acting at sites on Cdk4 and cyclin D1 that were also employed by p21$^{WAF1}$, we carried out peptide precipitation assays in the presence and absence of full length purified his-p21$^{WAF1}$ to find out if it competed with the peptides for binding.

The ability of p21$^{WAF1}$ to interfere with peptide 2 (A) and peptide 10 (B & C) binding to Cdk4 and/or cyclin D1 was determined by carrying out the peptide precipitation assay from reticulocyte lysates in the presence of 0, 0.5, 2 $\mu$g of p21$^{WAF1}$.

The data suggest that binding of p21$^{WAF1}$ protein to cyclin D1 and Cdk4 prevents binding of both peptide 2 and peptide 10. These data are open to two interpretations, (i) the peptides could be competing for binding at the same site as p21$^{WAF1}$, or (ii) binding of either p21$^{WAF1}$ or peptide could cause a conformational change in the cyclin or CDK preventing further binding. It is not clear from these experiments whether peptides 2 and 10 are acting at the same site(s). However the difference in the peptide precipitation data, indicates that at least one of the sites is unique, as peptide 10 can precipitate both Cdk4 and cyclin D1, whereas, peptide 2 can only precipitate cyclin D1.

Data to support the hypothesis that peptide 10 and p21$^{WAF1}$ protein compete for the same binding site, during kinase inhibition, employs the use of a peptide 10 mutant (containing a point mutation resulting in a change of R-A at residue 15 of peptide 10 which is equivalent to residue 155 of the full length protein) which loses >60% of its inhibitory activity (see below), but retains its binding function.

To determine if the inhibition of Cdk4 by p21$^{WAF1}$ could be relieved by the addition of a peptide 10 mutant, the R to A mutant (residue 15 of peptide 10) that was no longer an efficient inhibitor but still displayed partial binding activity, increasing concentrations of peptide (1, 5, 17 & 34 $\mu$M) were added to cyclin D1-Cdk4 GST-Rb phosphorylation assay in the presence of a fixed concentration of p21$^{WAF1}$ (50 $\mu$M)

The experiment showed that increasing concentrations of mutant peptide 10 were able to block the inhibitory activity of full length p21$^{WAF1}$ suggesting that peptide 10 is binding at a site(s) which blocks subsequent binding of p21$^{WAF1}$ and is therefore functioning through a similar mechanism to the full length protein.

The Inhibitory Peptides are not Cyclin D1-Cdk4 Substrates Unlike the p107 protein, which appears to inhibit Cdk4s ability to phosphorylate pRb by acting as an alternative substrate (Zhu et al., 1995), p21$^{WAF1}$ has not been reported to act as a substrate for the cyclin D1-Cdk4 complexes (and we confirm these observations FIG. 4). However, it is possible that by using p21$^{WAF1}$ based peptides, instead of full length protein, we have inadvertently generated phosphorylation sites which would not normally be exposed on the surface of the protein. Thus the peptides could be acting as competitive substrates as opposed to inhibitors of catalytic activity. Both peptide 2 and peptide 10 contain a number of possible phosphorylation sites, and we have been able to demonstrate that peptide 10 is a potential substrate for a number of protein kinases (data not shown), including protein kinase C (PKC) which was used as a control kinase (FIG. 4). In fact, neither peptide 2 nor peptide 10 were substrates for cyclin D1-Cdk4 under conditions where 2.4 nMol of $^{32}$P were incorporated per nMol of GST-Rb. However, under the same conditions peptide 10 was an extremely good substrate for PKC with 0.82 nMol of 32P being incorporated per nMol of peptide (FIG. 4). There was a low level of incorporation into peptide 2, but as this was also present in assays using lysate from uninfected insect cells it must be attributed to low levels of endogenous protein kinase(s). Thus, it appears that the peptide inhibitors are not competitive substrates, but, are acting to block catalytic activity in a mechanism similar to p21$^{WAF1}$.

The Peptides are not Efficient Inhibitors of Cyclin B-Cdc2 Kinase Activity

Harper et al. (1995) have shown that p21$^{WAF1}$ is not a universal CDK inhibitor, but that it displays selectivity for the G1 and S-phase cyclin-CDK complexes. When they compared the ability of p21$^{WAF1}$ to inhibit Cyclin B-Cdc2, which acts at the G2/M transition, and cyclin D2-Cdk4, which functions during G1, they found that the $I_{0.5}$ for inhibition of cyclin B-Cdc2 was >600-fold higher than the $I_{0.5}$ for inhibition of cyclin D2-Cdk4 using purified recombinant proteins. We looked at the effect of adding our two cyclin D1-Cdk4 inhibitory peptides to cyclin B-Cdc2 and Cdk2-cyclin E assays at concentrations up to 20 $\mu$M and found that neither peptide 2 nor peptide 10 had a significant effect on Cdc2-cyclin B histone H1 kinase activity. However, Cdk2-cyclin E was inhibited by peptide 10, showing that peptide 10 can inhibit other $G_1$ cyclin-Cdk complexes. Thus, the p21$^{WAF1}$ based peptide inhibitors appear to have equivalent specificity to the full length protein.

To determine if peptides 2 and 10 could inhibit cyclin B-Cdc2 and cyclin E-Cdk2 kinase activity assays were performed using Sf9 cell lysates which were co-expressing human cyclin B and Cdc2. The conditions were identical to those described in the Experimental Procedures for cyclin D1-Cdk4 except that histone H1 (0.5 μg/assay) was used as the substrate for cyclin B-Cdc2. Cyclin D1-Cdk4 cyclin B-Cdc2 and cyclin E-Cdk2 were assayed in the presence of increasing concentrations of peptide 2 (0.25, 3, 10 and 40 μM) and peptide 10 (0.1, 0.5, 5, 20 μM)

The Kinase Inhibitory Motif of Peptide 10 is Distinct from the PCNA Binding Site We have shown that peptide 10 is an extremely potent inhibitor of cyclin D1-Cdk4 activity, with an $I_{0.5}$ of 0.1 mM which is 20-fold more potent than peptide 2, a peptide derived from the region of p21$^{WAF1}$ previously associated with growth arrest (Chen et al.,1995; Nakanishi et al., 1995a). We have also shown that a peptide (peptide 4) which spans the CDK interaction site of p21$^{WAF1}$ (Goubin and Ducommun, 1995; Nakanishi et al., 1995a), although capable of binding to Cdk4 to form a stable complex, has no detectable activity as a cyclin D1-Cdk4 inhibitor. Peptide 10 therefore looks like the best candidate for the development of a small peptide mimetic with high efficacy. Peptide 10 has previously been shown to form a specific high-affinity and reversible interaction with PCNA (Ball and Lane, 1996) and this peptide is sufficient to partially inhibit the function of PCNA during SV40 replication giving 50% inhibition at a concentration of approximately 7 mM (Warbrick et al., 1995). The PCNA interaction domain of p21$^{WAF1}$ has been mapped and the important residues were found to be amino acids 144–151 (QTSMTDFY (SEQ ID NO:27); Warbrick et al., 1995; Ball and Lane, 1996). Although the extreme C-terminal peptide (peptide 11) has amino acid residues important for binding to and inhibiting Cdk4 (see FIG. 1 and 2), it cannot bind PCNA (Warbrick et al., 1995; Ball and Lane, 1996). These results indicate that the kinase inhibitory and PCNA binding motif in the C-terminus of p21$^{WAF1}$ are distinct, but it does not rule out the possibility that an interaction between p21$^{WAF1}$ and PCNA or cyclin/kinase may require some common amino acids. It is therefore important to identify the precise inhibitory motif within the C-terminus of p21$^{WAF1}$ and establish if it overlaps, or is distinct from, the PCNA interaction domain. To investigate this question we took two approaches; we synthesised, (i) a series of peptides that had been shifted by 4 amino acids in either direction along peptide 10 (size scan; FIG. 7), and (ii) a series of peptides based on peptide 10 where each residue was sequentially mutated to alanine (alanine scan; FIG. 6). The ability of the peptides, in each of these two series, to inhibit Cdk4 activity in vitro was then determined. Using the size scan, we found that the peptide inhibition activity required amino acids 156–160, while amino acids 148–155 were dispensable. This uncouples the kinase inhibitory motif from the PCNA binding motif.

With the alanine scan we defined the critical residues for inhibition showing that a stretch of just 5 amino acids were essential for activity, with a single conservative point is mutation at either of two hydrophobic residues completely abolishing peptide 10 inhibitory activity (FIG. 6). The essential amino acids are RRLIF (SEQ ID NO:12) amino acis 155–160) where the bold characters are essential for activity and the underlined residue contributes significantly to inhibitory activity.

When tested in the peptide precipitation assay, mutation of the first R of this motif to A (aa 155 of full length p21$^{WAF1}$) partially retained its ability to bind both Cdk4 and cyclin D1, whereas mutations of L or F to A significantly decreased the affinity for Cdk4 and cyclin D1, and mutations of the second R or the I had no effect on binding (data not shown). This is why the R-A mutant was used in competition assays. The fact that a single point mutation in either of two hydrophobic residues (the L or F residues) completely abolishes inhibitory activity, suggested that inhibition was due to a specific interaction at key hydrophobic residues. The mapping data also explains why both peptide 10 and peptide 11 are good inhibitors of cyclin D1-Cdk4 activity (FIG. 2) as they both contain the inhibitory motif. Thus, it appears that the inhibitory portion of peptide 10 does not overlap with the PCNA binding site as they have no amino acid residues in common.

A Single Amino Acid Substitution in Peptide 10 Makes it a More Potent Inhibitor thus Approaching the Specific Activity of Full Length p21$^{WAF1}$ Protein Whilst carrying out the alanine scan experiments we noticed that one of the mutant peptides (D-A at position 9 of peptide 10 or 149 of the full length protein; FIG. 6) appeared to make the peptide a better inhibitor of cyclin D1-Cdk4 activity. We determined the $I_{0.5}$ for this peptide and compared it with peptide 10, full length purified his-p21$^{WAF1}$, and a peptide derived from the tumour suppressor protein p16 INK4 which has recently been reported to inhibit cyclin D1-Cdk4 activity in vitro and to prevent cell cycle progression (Fahraeus et al, 1996). The D-A mutation decreases the $I_{0.5}$ from 100 nM to 46 nM (FIG. 7). Comparing this with the p16INK4-based peptide, which has an $I_{0.5}$ of 16.3 μM (FIG. 7), we have now produced a peptide which is approximately 350-fold more active as a Cdk4 inhibitory compound. In fact, we now begin to approach the potency of p21$^{WAF1}$ itself, which has an $I_{0.5}$ of 11 nM in the insect cell lysate assay (FIG. 7). This value is in the same range as the Ki of 40 nM for p21$^{WAF1}$ obtained for the inhibition of cyclin D1-Cdk4 in Sf9 cell lysates by Harper et al. (1995). Compared to full length protein, the mutant peptide 10 has only a 3.5-fold lower specific activity as a kinase inhibitor in crude lysates. Why mutating the D-A in this position, which is well out side the domain shown to be essential for activity, reduces the $I_{0.5}$ is not known. It seems likely that it involves the presentation of the inhibitory motif, rather than a direct role for this residue in inhibition, as this mutation does not appear to increase the affinity of the peptide for either Cdk4 or cyclin D1 (data not shown).

The results indicate that peptide 10 could be used as a model on which to base small peptide mimetics of p21$^{WAF1}$ and we have provided evidence that alterations in the peptides structure or presentation of the active residues may lead to the generation of a peptide inhibitor which approaches the potency of full length p21$^{WAF1}$ as a cyclin D-Cdk4 inhibitor.

Results for the C-terminal Peptide (Peptide 10)

An Eight Amino Acid Peptide is Sufficient to Inhibit Cyclin D-Cdk4 Activity

Having identified residues which appeared to be critical for the inhibition of cyclin D1-Cdk4 by peptide 10, we determined if these residues were sufficient for inhibition, or if they had to be presented within the context of a larqer peptide. Strikingly, the eight amino acid peptide, KRR-LIFSK (SEQ ID NO:23), retained the ability to completely inhibit cyclin D1-Cdk4 activity and prevent phosphorylation of pRb (FIG. 6). However, the $I_{0.5}$ for the truncated peptide was approximately 1000-fold higher than that of the full length peptide ($I_{0.5}$ for the truncated peptide was approximately 100 μM). This was not an unexpected result as other studies have shown loss of potency upon reducing the length of bio-active peptides. However, it may be possible to improve the peptide inhibitory activity by manipulating the non-essential residues in a manner defined by Lin et al (1995) in an elegant series of experiments aimed at minimising the atrial natriuretic peptide.

Peptide 10 Works in Cell Systems

The introduction of p21$^{WAF1}$ into human brain, lung and colon cancer cell lines leads to a suppression of cell growth (El-Deiry et al, 1993). In addition, during a radiation-induced $G_1$ arrest in human fibroblasts p21$^{WAF1}$ protein levels increase, in a p53-dependent manner, leading to potent inhibition of the $G_1$ cyclin-CDKs and failure of the cells to enter S-phase (Dulic et al, 1994; Harper et al, 1995). In order for peptide 10 to function as a realistic template for the design of novel anti-proliferative drugs it must be able to mimic p21$^{WAF1}$'s CKI activity as a growth suppressor in a cellular background. We and others have recently shown that a 16 amino acid sequence from the homeodomain of the Antennapedia protein can act as a carrier for peptides with biological activity, translocating them across the plasma membrane and allowing them to interact with their target molecules (Fahraeus et al, 1996; Hall et al, 1996). To determine if peptide 10 retained its biological activity when introduced into tissue culture cells, we synthesised it directly onto the carrier peptide and added it to a culture of proliferating asynchronous human kerotinocyte-derived HaCaT cells. The linked peptide (designated Peptide-I; FIG. 9) contained a mutation of M to A at position 7, thus abolishing its activity as a PCNA binding peptide (Warbrick et al, 1995; Ball and Lane, 1996), and allowed us to study PCNA-independent affects of the peptide on normal cell cycle.

Peptide-I was added to the culture media at a concentration of 25 μM, the cells were fixed 24 hours later, and then analysed by fluorescence-activated cell sorting (FACS). $G_1$-, S- and $G_2$-phase distribution of untreated and Peptide-I treated cells was assayed using bromodeoxyuracil (BrdU). The number of cells entering S-phase in the presence of Peptide-I was dramatically reduced and the $G_1$ population showed a concomitant increase. This suggests that Peptide-I mimics the ability of full length p21$^{WAF1}$ to act as a growth suppressor by inducing a $G_1$-cell cycle arrest.

In order to ascertain if Peptide-I was functioning as a growth inhibitor by preventing the phosphorylation of pRb in a manner analogues to p21$^{WAF1}$, we used serum starvation to produce a synchronous population of HaCaT cells. Peptide-I was added to the cells at the same time as they were released from serum starvation and samples from treated and untreated cells were taken over a 24 hour period. The phosphorylation status of pRb was monitored by a gel mobility shift assay. When serum was added to starved cells, pRb became hyperphosphylated between 12 and hours, but in the presence of Peptide-I pRb remained hypophosphorylated. Thus, Peptide I causes a $G_1$-arrest in human HaCaT cells by preventing the phosphorylation of pRb.

We took an identical experimental approach to introduce, (i) the bio-active truncated peptide 10 and (ii) a control peptide 10 which lacked essential residues for CDK inhibition, into HaCaT cells. We tound that Peptide-II effectively promoted a $G_1$-phase arrest and totally prevented the phosphorylation of pRb when added at 50μM (FIG. 9b). However Peptide-III, which lacked the last 4 amino acids of peptide 10 (LIFS) had no detectable effect on the ability of HaCaT cells to enter S-phase. It is interesting that the truncated peptide 10 when coupled to carrier peptide (Peptide-II) and introduced into cells is only 2-fold less active as a growth suppressor than Peptide-I (see above for in vitro data). Linking the truncated peptide 10 to the carrier peptide may promote a more favourable inhibitory conformation, as the $I_{0.5}$ for carrier linked truncated peptide 10 (Peptide-Il in vitro is approximately 50-fold less than that of the free peptide 10 (data not shown).

Peptide 10 was added to Rb negative cells, and the results support its mimicry of the full length protein, i.e. it can mimic its biolgical activity as a cell cycle inhibitor. Peptide 10 was found to cause cell cycle arrestin pRb negative, as well as pRb positive cells. Using Soas2 cells the introduction of peptide I (peptide 10 linked to penetratin and mutated to prevent PCNA binding) leads to an increase in the population of cells in G1 phase.

Discussion

Synthetic peptides or peptido-mimetics are proving to be useful in studying the biochemical regulation of enzymes and proteins, and also in providing models for the design of novel anti-proliferative agents targeted to the enzymatic pathways amplified or proteins activated in human tumours (Powis, 1992; Gibbs and Oliff, 1994). Peptides which have been shown to effectively target components of the cell cycle machinery include: FTI, which inhibit farnesyl protein transferase preventing the activation of Ras (Gibbs et al., 1994); Ras effector domain peptides, which can inhibit its biological function (Moodie and Wolfman, 1994; Rodriguez-Viciana et al., 1994); SH2/SH3 domain-harbouring polypeptides, which in theory should inhibit the growth of tumours with activated tyrosine kinases (Pawson and Schlessinger, 1993; Yu et al., 1994), and p16lNX4-derived peptides, which inhibit cyclin D-CDK complex activity and thereby activate pRb-dependent cell cycle arrest (Fahraeus et al., 1996).

Inactivation of the tumour suppressor protein p53 is a common event in the development of human neoplasia (Hollstein et al., 1991). The p53 protein is a key player in an inducible cell cycle checkpoint pathway activated in response to DNA-damage and nucleotide pool perturbation (Lane, 1992; Agarwal et al., 1995). Reactivation of this pathway could therefore provide a route to the discovery of novel anti-proliferative drugs. A variety of mechanisms could lead to the functional inactivation of the p53 pathway, including the inactivation of downstream effector molecules of p53, such as the cyclin-kinase inhibitor p21WAP1 (Deng et al., 1995; Waldman et al., 1995). Recent developments have shown that reactivation of the p53 pathway in some human tumours may be possible by activating the biochemical function of the endogenous mutant p53 protein (Halazonetis and Kandil, 1993; Hupp et al., 1993), possibly using small peptides as leads for drug design (Hupp et al., 1995) or by reintroducing the wild type p53 gene using adenovirus vectors (Eastham et al., 1995). However, in general, the pharmacological restoration of biochemical function to a protein that has lost its normal activity through mutation of its amino acid sequence is more difficult than the inhibition of a biochemical function (Gibbs and Oliff, 1994). Thus, it may prove more productive to take alternative approaches to restore activity to the p53 pathway such as mimicking the inhibitory activity of the downstream effector molecule p21WAF1, which can by itself mediate growth arrest primarily through its interaction with the G1 cyclin-CDKs (El-Deiry et al., 1993; Eastham et al., 1995; Harper et al., 1995).

Determining the minimal domain of p21$^{WAF1}$ that can inhibit CDK function and whether such a domain can function in isolation with high efficiency are two important goals which must be achieved in order to determine whether p21$^{WAF1}$ will prove to be a realistic template for use in anti-proliferative drug design research. Prior to our studies, the minimal sequence of p21$^{WAF1}$ shown to inhibit CDK function in vitro was the N-terminal domain (residues 1–75) (Luo et al., 1995). Whilst peptides derived from this N-terminal domain have recently been shown to antagonise the ability of p21$^{WAF1}$ to inhibit cyclin E-Cdk2 complex activity suggesting that this domain interacts with the kinase (Chen et al., 1996), no data on the direct interaction of small peptides with either cyclin or CDK has previously been presented. In addition, no evidence existed to suggest that a small peptide derived from p21$^{WAF1}$ would in fact be biologically active as a CDK inhibitor. As the cyclin D1-Cdk4 complexes and related isoforms are essential for progression through G1-phase, we have used a series of small synthetic peptides based on the sequence of p21$^{WAF1}$ to, (i) determine whether Cdk4 inhibitory peptide-mimetics exist and if they are of high efficacy, and (ii) probe the mechanism by which the p21$^{WAF1}$ protein inhibits cyclin D1-Cdk4 activity.

A Model for the Inhibition of Cyclin D1-Cdk4 by p21$^{WAF1}$

Two distinct peptides from the N-terminal domain of p21$^{WAF1}$ interacted with either Cdk4 or cyclin D1 to form stable complexes. One peptide bound to Cdk4 but did not inhibit its activity, while the second bound specifically to cyclin D1 and had potent inhibitory effects on cyclin D1-Cdk4 activity. The Cdk4 binding peptide 4 (residues 46–65) corresponded to a putative Cdk2 binding domain of p$_{21}$WAF1 previously defined using p21$^{WAF1}$ deletion constructs (Nakanishi et al., 1995a) and alanine mutation analysis (Goubin and Ducommun, 1995). We have established that this region of p21$^{WAF1}$ is, in fact, directly involved in CDK binding, yet it has no Cdk4 inhibitory activity (FIGS. 2 and 3). These data explain why certain N-terminally deleted p21$^{WAF1}$ constructs, which still contain the CDK binding site, fail to efficiently inhibit cell growth (Nakanishi et al., 1995a).

The second N-terminal peptide, which bound to cyclin D1, potently inhibited cyclin D1-Cdk4 activity through a novel mechanism (see below). The mechanism of p21$^{WAF1}$ inhibition of cyclin-CDK complexes is poorly understood, as it has not been clear whether p21$^{WAF1}$ protein inhibits by cyclin and/or kinase subunit binding. Cdk2 binds very weakly to p21WAF1 in the absence of cyclin, the affinity of the G1-CDKs for p21$^{WAF1}$ being greatly increased if the CDK is associated with a cyclin (Harper et al., 1995), suggesting that cyclins play an important role in p21$^{WAF1}$ inhibition of CDK activity. However, whether a CKI, such as p21$^{WAF1}$ and p27KIP1, can interact directly with cyclin is in dispute (Toyoshima and Hunter, 1994; Harper et al., 1995). A recent study however, suggested that p21$^{WAF1}$ can interact directly with a number of cyclins in the absence of CDK (Fotedar et al., 1996). We show here that a small peptide composed of residues 16–35 (peptide 2) forms a stable complex with cyclin D1 and that this peptide alone is a potent inhibitor of Cdk4 activity, with an I$_{0.5}$ of 2 mM. This peptide falls within the growth suppressor region (residues 17–71), described by Nakanishi et al. (1995a). This is the first time that a putative cyclin binding site on p21$^{WAF1}$ has been identified and that a small synthetic peptide representing this domain has been shown to be sufficient to mimic the full length p21$^{WAF1}$ protein as a CDK inhibitor.

The fact that cyclin D1-Cdk4 activity can be inhibited by interaction with the cyclin subunit alone, suggests either (i) that conformational changes in cyclin D1 can lead to the inhibition of Cdk4 catalytic activity, (ii) that peptide 2 interferes with the interaction of cyclin D1 with Cdk4 or (iii) that peptide 2 interferes with the interaction-of cyclin D1-Cdk4 with its substrate pRb.

Prospects for the design of small molecular mimetics of p21$^{WAF1}$ are more viable given that the cyclin D1-binding peptide alone can inhibit kinase function, indicating that the prior presence of one p21$^{WAF1}$ protein binding to the kinase subunit is not required for inhibition of kinase function. In addition, the amino acid residues that are conserved between p21$^{WAF1}$ and its close relative p27KIP1 (Polyak et al., 1994; Toyoshima and Hunter, 1994) are clustered within the N-terminal domain, with the regions corresponding to peptides 2 (65% identical) and peptide 4 (50% identical) containing the majority of the conserved amino acids. This suggests that inhibition of Cdk4 activity by interaction with the cyclin D subunit may be a common mechanism employed by both p21$^{WAF1}$ and p27KIP1.

A Novel p21$^{WAF1}$ C-Terminal Cyclin D1-Cdk4 Inhibitory Domain During the course of our studies we also found that a peptide (peptide 10) from the C-terminal domain of p21$^{WAF1}$ was a potent inhibitor of cyclin D1-Cdk4 activity in vitro. The inhibitory motif was identified and was distinct from the PCNA interacting site, which also resides in the C-terminal domain of p21$^{WAF1}$ (Chen et al., 1995; Luo et al., 1995; Warbrick et al., 1995; Ball and Lane, 1996). Our results are in contrast to previous studies which have found that cyclin-Cdk2 inhibitory activity is confined solely to the N-terminal domain of p21$^{WAF1}$, when each half is expressed separately (Chen et al., 1995; Luo et al., 1995). The reasons for this discrepancy may include: (i) the use of C-terminally his-tagged p21$^{WAF1}$ in expression vectors for purifying p21$^{WAF1}$ constructs (Luo et al., 1995), which may have affected the local structure at the C-terminus of p21$^{WAF1}$; (ii) the transfection of constructs containing only the C-terminal half of p21$^{WAF1}$ (Chen et al., 1995; Luo et al., 1995) this may make folding into the correct native conformation difficult precluding identification of the novel inhibitory domain; (iii) by using peptides, rather that the C-terminal constructs or full length p21$^{WAF1}$ protein, we may have exposed sites which would not be solvent exposed in native full length p21$^{WAF1}$ protein; (iv) it is possible that there may be subtle differences in the mechanism(s) used by p21$^{WAF1}$ to inhibit cyclin-Cdk2 complexes and cyclin D1-Cdk4. Whether, the C-terminal inhibitory motif defines a novel physiologically relevant regulatory site on p21$^{WAF1}$ is currently being addressed. However, the potency of peptide 10 (I$_{0.5}$=0.1 mM, only 10-fold lower than full length p21$^{WAF1}$ protein in these assays) and its ability to completely inhibit cyclin D1-Cdk4, suggests to us that further studies on this region of full length p21$^{WAF1}$ will be well worth pursuing.

Peptide 10 represents a potentially exciting lead for drug design as it is by far the most potent peptide inhibitor of CDK activity discovered to date, being>150-fold better than the recently identified peptide mimetic of p16INK4 (Fahraeus et al., 1996) and 20-fold better than the N-terminal inhibitory p21$^{WAF1}$-derived-peptide which we have described. The fact that the residues important for inhibitory activity are confined to a stretch of just five amino acids, suggests that contact at a single interface is sufficient to produce a highly potent inhibitor of the cyclin D1-Cdk4 activity, making this a realistic template for the design of small molecules which mimic p21$^{WAF1}$ activity.

The fact that peptide 10 retains inhibitory activity when reduced to just eight amino acids (KRRLIFSK)(SEQ ID NO: 23) improves its appeal as a template for rational drug design. In general protein-protein interfaces are relatively large relying on the participation of between 10–30 contact side chains on each interface, with each region of contact often being composed of residues which are dispersed throughout the primary amino acid sequence (Davies et al, 1990; de Vos et al, 1992). However, there is evidence that in some cases only a small subset of these side chains need to be contacted for efficient binding to occur (Kelley and O'connel, 1993, Cunningham and Wells, 1994; Clackson and Wells, 1995). The discovery that a single eight amino acid peptide is alone sufficient to inhibit the activity of a critical $G_1$-cyclin-CDK preventing pRb phosphorylation and producing a $G_1$-cell cycle arrest in tissue culture cell systems, suggests that interaction at only a small subset of contact side chains is necessary for potent inhibition of cyclin D1-cdk4 activity at the $G_1$-S phase boundary. This makes cyclin D1-Cdk4 a realistic and exciting target for the design of small synthetic compounds which can at act as anti-proliferative agents.

References

All references mentioned anywhere in this document are hereby incorporated by reference.

Agarwal, et al. (1995). *Proc. Natl. Acad. Sci. U.S.A.,* 92: 8493–8497.
Baldin, et al. (1993). *Genes Dev.,* 7: 812–821.
Ball, K. L. and Lane, D. P. (1996). Biochem., 237: 854–861.
Buckbinder, et al. (1995). *Nature,* 377: 646–649.
Chen, et al. (1996). *Oncogene,* 12: 595–607.
Chen, et al. (1995). *Nature,* 374: 386–388.
Clackson, T. and Wells J. A. (1995). *Science,* 267: 383–386.
Clarke, et al. (1993). *Nature,* 362: 849–852.
Cunningham, B. C. and Wells, J. A. (1994). *J. Mol. Biol.,* 234: 554–563.
Davies, et al. (1990). *Rev. Biochein.,* 59: 439–473.
Deng, et al. (1995). *Cell,* 82: 675–684.
de Vos, et al. (1992). *Science,* 255: 306–312.
Dulic, et al.(1994). *Cell,* 76: 1013–1023.
Eastham, et al. (1995). *Cancer Res.,* 55: 5151–5155.
El-Deiry, et al. (1993). *Cell,* 75: 817–825.
Fahraeus, et al. (1996). *Curr. Biol.,* 6: 84–91.
Flores-Rozas, et al. (1994). *Proc. Natl. Acad. Sci. U.S.A.,* 91: 8655–8659.
Gibbs, J. B. and Oliff, A. (1994). *Cell,* 79: 193–198.
Gibbs, et al. (1994). *Cell,* 77: 175–178.
Goubin, F. and Ducommun, B. (1995). *Oncogene,* 10: 2281–2287.
Gu, et al. (1993). *Nature,* 371: 257–261.
Halazonetis, T. D. and Kandil, A. N. (1993). *EMBO J.,* 12: 5057–5064.
Hall, et al. (1996). *Curr. Biol.,* 6: 580–587.
Harper, et al. (1993). *Cell,* 75: 805–816.
Harper, et al. Tsai, L-H:, Zhang, P., Dobrowolski, C. B., Connell-Crowley, et al. (1995). *Cell,* 6: 387–400.
Hollstein, et al. (1991). *Science,* 253: 49–53.
Hupp, et al. (1993). *Nucl. Acids Res.,* 21: 3167–3174.
Hupp, et al. (1995). *Cell,* 83: 337–345.
Kastan, et al. (1991). *Cancer Res.,* 51: 6304–6311.
Kastan, et al. (1992). *Cell,* 71: 587–597.
Kearsey, et al. (1995). *Science,* 270: 1004–1005.
Kelley, R. F. and O'Connell, M. P. (1993). *Biochemistry,* 32: 6828–6835.
Lane, D. P. (1992). *Nature,* 358: 15–16.
Lowe, et al. (1993). *Nature,* 362: 847–849.
Luo, et al. (1995). *Nature,* 375: 159–161.
Lu, X. and Lane, D. P. (1993). *Cell,* 75: 765–778.
Merritt, et al. (1994). *Cancer Res.,* 54: 614–617.
Miyashita, T. and Reed, J. C. (1995). *Cell,* 80: 293–299.
Momand, et al. (1992). *Cell,* 69: 1237–1245.
Moodie, S. A. and Wolfman, A. (1994). *Trends Genet.,* 10: 44–48.
Nakanishi, et al. (1995a). *EMBO J.,* 14: 555–563.
Nakanishi, et al. (1995b).*J. Biol. Chem.,* 270: 17060–17063.
Pawson, T. and Schlessinger, J. (1993). *Current Biology,* 3: 434–432.
Picksley, et al. (1994). *Oncogene,* 9: 2523–2529.
Pietenpol, et al. (1994). *Proc. Natl. Acad. Sci. U.S.A.,* 91: 1998–2002.
Pines, J. (1995). *Nature,* 376: 294–295.
Polyak, et al. (1994). *Cell,* 78: 59–66.
Powis, G. (1992). *Trends Pharmacol. Sci.,* 12: 188–194.
Rodriguez-Viciana, et al. (1994). *Nature,* 370: 527–532.
Sherr, C. (1994). *Cell.,* 79: 551–555.
Smythe, et al. (1988). *EMBO J.,* 7: 2681–2686.
Toyoshima, H. and Hunter, T. (1994). *Cell,* 78: 67–74.
Waldman, et al. (1995). *Cancer Research,* 55: 5187–5190.
Warbrick, et al. (1995). *Curr. Biol.,* 5: 275–282.
Waga, et al. (1994). *Nature,* 369: 574–578.
Yu, et al. (1994). *Cell,* 76: 933–945.
Xiong, et al. (1993). *Nature,* 366: 701–704.
Zhu, et al. (1995). *Genes & Development,* 9: 1740–1752.

What is claimed is:

1. A method for identifying a compound which modulates binding between p21 and cyclin D1, the method including:
    (a) bringing into contact a first substance comprising a peptide fragment of 40 amino acids or less of p21, the peptide fragment comprising an amino acid sequence selected from the group consisting of:
    KACRRLFGPVDSEQLSRDCD (peptide 2) (SEQ ID NO:2);
    KRRQTSMTDFYHSKRRLIFS (peptide 10) (SEQ ID NO:10), wherein the amino acid D may be replaced by any amino acid;
    KRRQTSATDFYHSKRRLIFS (SEQ ID NO:28);
    TSMTDFYHSKRRLIFSKRKP (peptide 11) (SEQ ID NO:11); and
    KRRLIFSK (SEQ ID NO:23), wherein K, R, I or S may be replaced by any amino acid;
    with a second substance comprising cyclin D1 or a fragment thereof, and a test compound, under conditions wherein, in the absence of the test compound being an inhibitor of binding of said first and second substances, said first substance and said second substance bind; and
    (b) determining binding between said first substance and said second substance.

2. A method for identifying a compound which modulates binding between p21 and Cdk4, the method including:
    (a) bringing into contact a first substance which comprises a peptide fragment of 40 amino acids or less of p21, the peptide fragment comprising an amino acid sequence selected from the group consisting of:
    RERWNFDFVTETPLEGDFAW (peptide 4) (SEQ ID NO:4);
    KRRQTSMTDFYHSKRRLIFS (peptide 10) (SEQ ID NO:10), wherein D may be replaced by any amino acid;
    KRRQTSATDFYHSKRRLIFS (SEQ ID NO:28);
    TSMTDFYHSKRRLIFSKRKP (peptide 11) (SEQ ID NO:11); and
    KRRLIFSK (SEQ ID NO:23), wherein K, R, I or S may be replaced by any amino acid,
    with a second substance comprising Cdk4 or a fragment thereof, and a test compound, under conditions wherein, in the absence of the test compound being an inhibitor of binding of said first and second substances, said first substance and said second substance bind; and
    (b) determining binding between said first substance and said second substance.

3. A method for identifying a compound which modulates binding between p21, cyclin D1 and Cdk4, the method including:
    (a) bringing into contact a first substance which comprises a peptide fragment of 40 amino acides or less of p21, the peptide fragment comprising an amino acid sequence selected from the group consisting of:
    KACRRLFGPVDSEQLSRDCD (peptide 2) (SEQ ID NO:2);
    KRRQTSMTDFYHSKRRLIFS (peptide 10) (SEQ ID NO:20), wherein D may be replaced by any amino acid;
    KRRQTSATDFYHSKRRLIFS (SEQ ID NO:28);
    TSMTDFYHSKRRLIFSKRKP (peptide 11) (SEQ ID NO:11); and
    KRRLIFSK (SEQ ID NO:23), wherein K, R, I or S may be replaced by any amino acid, with a second substance comprising cyclin D1 or a fragment thereof, a third substance comprising Cdk4 or a fragment thereof, and a test compound, under conditions wherein, in the absence of the test compound being an inhibitor of binding of said first, and second substances, said first, second and third substances bind; and
    (b) determining binding between the first, second and third substances.

4. A method for identifying a compound which modulates binding between p21 and cyclin D1, the method including:
(a) bringing into contact a peptide fragment of 40 amino acids or less p21, the peptide fragment comprising an amino acid sequence selected from the group consisting of:
KACRRLFGPVDSEQLSRDCD (peptide 2) (SEQ ID NO:2);
KRRQTSMTDFYHSKRRLIFS (peptide 10) (SEQ ID NO:10), wherein D may be replaced by any amino acid;
KRRQTSATDFYHSKRRLIFS (SEQ ID NO:28);
TSMTDFYHSKRRLIFSKRKP (peptide 11) (SEQ ID NO:11); and
KRRLIFSK (SEQ ID NO:23), wherein K, R, I or S may be replaced by any amino acid;
with cyclin D1 and a test compound under conditions wherein in the absence of the test compound said peptide fragment and cyclin D1 bind; and
(b) determining binding between said peptide fragment or derivative and cyclin D1 in the presence of said test compound.

5. A method for identifying a compound which modulates binding between p21 and Cdk4, the method including:
(a) bringing into contact a peptide fragment of 40 amino acids or less of p21, the peptide fragment comprising an amino acid sequence selected from the group consisting of:
RERWNFDFVTETPLEGDFAW (peptide 4) (SEQ ID NO:4);
KRRQTSMTDFYHSKRRLIFS (peptide 10) (SEQ ID NO:10); wherein D may be replaced by any amino acid;
KRRQTSATDFYHSKRRLIFS (SEQ ID NO:28);
TSMTDFYHSKRRLIFSKRKP (peptide 11) (SEQ ID NO:11); and
KRRLIFSK (SEQ ID NO:23), wherein K, R, I or S may be replaced by any amino acid, with Cdk4 and a test compound under conditions wherein in the absence of the test compound said fragment and Cdk4 bind; and
(b) determining binding between said peptide fragment or derivative and Cdk4 in the presence of said test compound.

6. A method for identifying a compound when modulates binding between p21, cyclin D1 and Cdk4, the method including:
(a) bringing into contact a peptide fragment of 40 amino acids or less p21, the peptide fragment comprising an amino acid sequence selected from the group consisting of:
KACRRLFGPVDSEQLSRDCD (peptide 2) (SEQ ID NO:2);
KRRQTSMTDFYHSKRRLIFS (peptide 10) (SEQ ID NO:10), wherein D may be replaced by any amino acid;
KRRQTSATDFYHSKRRLIFS (SEQ ID NO:28);
TSMTDFYHSKRRLIFSKRKP (peptide 11) (SEQ ID NO:11); and
KRRLIFSK (SEQ ID NO:23), wherein K, R, I or S may be replaced by any amino acid;
with a cyclin D1, Cdk4 and a test compound under conditions wherein in the absence of the test compound said peptide fragment, cyclin D1 and Cdk4 bind; and
(b) determining binding between said peptide fragment or derivative, cyclin D1, and Cdk4 in the presence of the test compound.

7. The method according to claim 5, wherein the peptide fragment of p21 comprises the amino acid sequence of peptide 4 (SEQ ID NO:4).

8. The method according to claim 1, 2, 3 or 4–6, wherein the peptide fragment of p21 comprises the amino acid sequence of peptide 10 (SEQ ID NO:10), wherein the amino acid D has been replaced by any amino acid.

9. The method according to claim 1, 3, 4 or 6, wherein the peptide fragment of p21 comprises the amino acid sequence of peptide 2 (SEQ ID NO:2).

10. The method according to claim 1, 2, 3 or 4–6 wherein the peptide fragment of p21 comprises the amino acid sequence KRRLIFSK (SEQ ID NO: 23), wherein at least one of the amino acid residue selected from the group consisting of R and I have been replaced by any amino acid.

11. The method according to claim 1, 2, 3 or 4–6, wherein the peptide fragment of p21 comprises the amino acid sequence of peptide 10 (SEQ ID NO:10).

12. The method according to claim 1, 2, 3 or 4–6, wherein the peptide fragment of p21 comprises the amino acid sequence KRRLIFSK (SEQ ID NO:23).

13. The method according to claim 1, 2, 3 or 4–6, wherein the peptide fragment of p21 comprises the amino acid sequence of peptide 11 (SEQ ID NO:11).

14. The method according to claim 1, 2, 3 or 4–6, further comprising testing the ability of the compound to modulate a p21-mediated effect on Cdk4 activity.

15. The method according to claim 14 wherein RB phosphorylation is tested.

16. The method according to claim 1, 2, 3 or 4–6 wherein induction of G1 cell-cycle arrest is tested.

17. A method comprising obtaining a compound which modulates the binding between p21 and cyclin D1 in accordance with claim 1 or 4, further comprising formulating the compound into a composition including at least one additional component.

18. A method comprising obtaining a compound which modulates the binding between p21 and cyclin Cdk4 in accordance with claim 2 or 5, further comprising formulating the compound into a composition including at least one additional component.

19. A method comprising obtaining a compound which modulates the binding between p21, cyclin D1 and Cdk4 in accordance with claim 3 or 6, further comprising formulating the compound into a composition including at least one additional component.

20. The method of claim 1, 2, 3 or 4–6, wherein the peptide fragment of p21 is about 40 amino acids or less.

21. The method of claim 1, 2, 3 or 4–6, wherein the peptide fragment of p21 is about 35 amino acids or less.

22. The method of claim 1, 2, 3 or 4–6, wherein the peptide fragment of p21 is about 30 amino acids or less.

23. The method of claim 1, 2, 3 or 4–6, wherein the peptide fragment of p21 is about 25 amino acids or less.

24. The method of claim 1, 2, 3 or 4–6, wherein the peptide fragment of p21 is about 20 amino acids or less.

25. The method of claim 1, 2, 3 or 4–6, wherein the peptide fragment of p21 is about 10 amino acids or less.

26. The method according to claim 8, wherein the amino acid D has been replaced by A.

* * * * *

UNITED STATES PATENT AND TRADEMARK OFFICE
CERTIFICATE OF CORRECTION

PATENT NO. : 6,962,792 B2  
APPLICATION NO. : 09/180269  
DATED : November 8, 2005  
INVENTOR(S) : Kathryn Lindsay Ball et al.

It is certified that error appears in the above-identified patent and that said Letters Patent is hereby corrected as shown below:

Column 44,  
Line 47, replace "acides" with -- acids --.  
Line 53, replace "NO:20" with -- NO:10 --.  
Line 58, there should be a new paragraph starting after "acid,".  
Line 64, replace "said first, and second substances," with -- said first, second and third substances, --.  
Line 66, replace "the" with -- said --.

Column 45,  
Line 4, between "less" and "p21," insert -- of --.  
Line 33, replace ";" with -- , --.  
Line 39, there should be a new paragraph starting after "acid,".

Column 46,  
Line 2, remove the "," between "cyclin D1" and "and".  
Line 18, replace "have" with -- has --.  
Line 41, remove "cyclin".

Signed and Sealed this

Twentieth Day of June, 2006

JON W. DUDAS  
*Director of the United States Patent and Trademark Office*